US008273842B2

(12) United States Patent
Ichiryu et al.

(10) Patent No.: US 8,273,842 B2
(45) Date of Patent: Sep. 25, 2012

(54) PROCESS FOR PRODUCTION OF CYCLIC POLYORGANOSILOXANE, CURING AGENT, CURABLE COMPOSITION, AND CURED PRODUCT OF THE CURABLE COMPOSITION

(75) Inventors: Yoshikatsu Ichiryu, Settsu (JP); Masayuki Fujita, Settsu (JP)

(73) Assignee: Kaneka Corporation, Osaka (JP)

( * ) Notice: Subject to any disclaimer, the term of this patent is extended or adjusted under 35 U.S.C. 154(b) by 118 days.

(21) Appl. No.: 12/741,697

(22) PCT Filed: Nov. 7, 2008

(86) PCT No.: PCT/JP2008/070350
§ 371 (c)(1),
(2), (4) Date: May 6, 2010

(87) PCT Pub. No.: WO2009/060958
PCT Pub. Date: May 14, 2009

(65) Prior Publication Data
US 2010/0267919 A1    Oct. 21, 2010

(30) Foreign Application Priority Data
Nov. 9, 2007    (JP) ................................. 2007-292451

(51) Int. Cl.
*C08G 77/06* (2006.01)
*C08L 83/04* (2006.01)

(52) U.S. Cl. .......... 528/31; 525/477; 525/478; 525/479; 528/15; 528/32

(58) Field of Classification Search .................. None
See application file for complete search history.

(56) References Cited

U.S. PATENT DOCUMENTS

| | | | |
|---|---|---|---|
| 2,624,721 A | 1/1953 | Hatcher et al. | |
| 3,159,601 A | 12/1964 | Ashby | |
| 3,159,662 A | 12/1964 | Ashby | |
| 3,220,972 A | 11/1965 | Lamoreaux | |
| 3,439,014 A | 4/1969 | Patton et al. | |
| 3,516,946 A | 6/1970 | Scotia | |
| 3,714,213 A | 1/1973 | Miller et al. | |
| 3,892,643 A | 7/1975 | Tanaka et al. | |
| 4,447,630 A | 5/1984 | Williams, Jr. | |
| 4,855,378 A | 8/1989 | Pradi et al. | |
| 4,895,967 A | 1/1990 | Crivello et al. | |
| 4,902,731 A | 2/1990 | Leibfried | |
| 4,943,601 A | 7/1990 | Dinallo | |
| 5,077,134 A | 12/1991 | Leibfried | |
| 5,086,148 A * | 2/1992 | Jochum et al. | 528/15 |
| 5,101,029 A | 3/1992 | Stapp et al. | |
| 5,166,298 A | 11/1992 | Friedmann et al. | |
| 5,204,384 A | 4/1993 | Matsushita et al. | |
| 5,204,408 A | 4/1993 | Konno et al. | |
| 5,208,289 A | 5/1993 | Takarada et al. | |
| 5,296,298 A | 3/1994 | Fujimoto et al. | |
| 5,298,589 A * | 3/1994 | Buese et al. | 528/21 |
| 5,340,872 A | 8/1994 | Inoue et al. | |
| 5,391,678 A | 2/1995 | Bard et al. | |
| 5,409,995 A | 4/1995 | Iwahara et al. | |
| 5,466,728 A * | 11/1995 | Babcock et al. | 523/179 |
| 5,523,374 A | 6/1996 | Bard et al. | |
| 5,580,925 A | 12/1996 | Iwahara et al. | |
| 5,605,726 A | 2/1997 | Gibbons et al. | |
| 5,623,030 A | 4/1997 | Tsumura et al. | |
| 5,684,110 A | 11/1997 | Kawamura | |
| 5,691,433 A | 11/1997 | Kotani et al. | |
| 5,691,435 A | 11/1997 | Herzig et al. | |
| 5,773,532 A | 6/1998 | Okaniwa et al. | |
| 5,981,679 A | 11/1999 | Takei et al. | |
| 5,993,690 A | 11/1999 | Kondo et al. | |
| 6,093,782 A | 7/2000 | Herzig et al. | |
| 6,129,980 A | 10/2000 | Tsukada et al. | |
| 6,187,890 B1 | 2/2001 | Fehn et al. | |
| 6,262,289 B1 | 7/2001 | Ouchi | |
| 6,303,728 B1 | 10/2001 | Hagimori et al. | |

(Continued)

FOREIGN PATENT DOCUMENTS

CA    2297068    11/1999

(Continued)

OTHER PUBLICATIONS

English translation of the International Preliminary Report on Patentability (Chapter 1) of PCT Application No. PCT/JP2008/070350.
International Search Report for PCT/JP2008/070350, mailed Jan. 6, 2009.
Non-Final Office Action in U.S. Appl. No. 10/239,777, all pages, mailed Jul. 2, 2004.
Final Office Action in U.S. Appl. No. 10/239,777, all pages, mailed Feb. 15, 2005.
Advisory Action in U.S. Appl. No. 10/239,777, all pages, mailed Jul. 29, 2005.
Non-Final Office Action in U.S. Appl. No. 10/239,777, all pages, mailed Dec. 30, 2005.
Non-Final Office Action in U.S. Appl. No. 10/239,777, all pages, mailed Aug. 8, 2006.

(Continued)

*Primary Examiner* — Marc Zimmer
(74) *Attorney, Agent, or Firm* — Nixon & Vanderhye P.C.

(57) ABSTRACT

An object of the invention is to provide a curing agent and a curable composition capable of forming a cured product, which is applicable for optical material and which has excellent heat and light transparency and crack resistance, and a cured product obtained by curing the same. Moreover, an object of the invention is to provide a method for producing with use of the components of the curing agent a cyclic polyorganosiloxane having a specific structure, in a selective manner and in high yield. In order to attain the objects, a curable composition including, as essential components, (A) an organic compound including at least two carbon-carbon double bonds that are reactive with a SiH group, (B) a compound having at least two SiH groups per molecule, and (C) a hydrosilylation catalyst, uses a modified polyorganosiloxane compound having at least two SiH groups per molecule as the compound having at least two SiH groups, which modified polyorganosiloxane compound is a reaction product of a specific cyclic polyorganosiloxane.

28 Claims, No Drawings

U.S. PATENT DOCUMENTS

| | | | |
|---|---|---|---|
| 6,346,553 B1 * | 2/2002 | LeGrow et al. | 516/55 |
| 6,355,946 B1 | 3/2002 | Ishinaga | |
| 6,592,999 B1 | 7/2003 | Anderson et al. | |
| 6,791,259 B1 | 9/2004 | Stokes et al. | |
| 7,371,462 B2 * | 5/2008 | Tsumura et al. | 428/447 |
| 7,470,457 B2 | 12/2008 | Tsumura et al. | |
| 7,560,145 B2 * | 7/2009 | Ouchi et al. | 428/1.1 |
| 7,785,715 B2 * | 8/2010 | Tsumura et al. | 428/447 |
| 2002/156186 A1 | 10/2002 | Bublewitz et al. | |
| 2003/0144420 A1 | 7/2003 | Tsumura et al. | |
| 2003/0232222 A1 | 12/2003 | Anderson et al. | |
| 2004/0126504 A1 | 7/2004 | Ouchi et al. | |
| 2005/0042463 A1 | 2/2005 | Anderson et al. | |
| 2005/0209400 A1 | 9/2005 | Tsumura et al. | |
| 2006/0223963 A1 | 10/2006 | Shinbo | |
| 2007/0135590 A1 * | 6/2007 | Kotani et al. | 525/479 |

FOREIGN PATENT DOCUMENTS

| | | |
|---|---|---|
| EP | 803 529 | 10/1997 |
| EP | 1 369 458 | 12/2003 |
| EP | 1 505 121 | 2/2005 |
| JP | 33-2149 | 3/1958 |
| JP | 45-15036 | 5/1970 |
| JP | 50-100 | 1/1975 |
| JP | 54-13480 | 5/1979 |
| JP | 54-74900 | 6/1979 |
| JP | 59-155483 | 9/1984 |
| JP | 61-118746 | 6/1986 |
| JP | 62-20733 | 1/1987 |
| JP | 3-14838 | 1/1991 |
| JP | 3-95266 | 4/1991 |
| JP | 3-247686 | 11/1991 |
| JP | 3-277645 | 12/1991 |
| JP | 5-140459 | 6/1993 |
| JP | 5-295270 | 11/1993 |
| JP | 5-320516 | 12/1993 |
| JP | 6-80882 | 3/1994 |
| JP | 6-207104 | 7/1994 |
| JP | 7-3030 | 1/1995 |
| JP | 7-62103 | 3/1995 |
| JP | 7-149899 | 6/1995 |
| JP | 07-242678 | 9/1995 |
| JP | 07-316167 | 12/1995 |
| JP | 8-157720 | 6/1996 |
| JP | 8-183934 | 7/1996 |
| JP | 9-291214 | 11/1997 |
| JP | 9-302095 | 11/1997 |
| JP | 9-316293 | 12/1997 |
| JP | 10-003270 | 6/1998 |
| JP | 10-176110 | 6/1998 |
| JP | 11-269271 | 10/1999 |
| JP | 2000-63672 | 2/2000 |
| JP | 2000-086766 | 3/2000 |
| JP | 2000-124475 | 4/2000 |
| JP | 2000-136275 | 5/2000 |
| JP | 2000-183407 | 6/2000 |
| JP | 2000-231003 | 8/2000 |
| JP | 2000-344895 | 12/2000 |
| JP | 2001-011210 | 1/2001 |
| JP | 2001-019742 | 1/2001 |
| JP | 2001-118865 | 4/2001 |
| JP | 2001-207059 | 7/2001 |
| JP | 2002-80733 | 3/2002 |
| JP | 2002-194215 | 7/2002 |
| JP | 2002-217459 | 8/2002 |
| JP | 2002-235005 | 8/2002 |
| JP | 3354973 | 9/2002 |
| JP | 2002-314140 | 10/2002 |
| JP | 2002-317048 | 10/2002 |
| JP | 2002-324920 | 11/2002 |
| JP | 2002-338833 | 11/2002 |
| JP | 2003-113310 | 4/2003 |
| JP | 2003-128921 | 5/2003 |
| JP | 2003-261770 | 9/2003 |
| JP | 2003-261783 | 9/2003 |
| JP | 2003-268239 | 9/2003 |
| JP | 2003-292568 | 10/2003 |
| WO | 99/24509 | 5/1999 |
| WO | 01/81475 | 11/2001 |
| WO | WO 02/53648 * | 6/2002 |
| WO | WO 03/091338 * | 11/2003 |
| WO | WO 2004/076585 * | 9/2004 |

OTHER PUBLICATIONS

Final Office Action in U.S. Appl. No. 10/239,777, all pages, mailed Apr. 5, 2007.
Non-Final Office Action in U.S. Appl. No. 10/239,777, all pages, mailed Oct. 9, 2007.
Final Office Action in U.S. Appl. No. 10/239,777, all pages, mailed May 29, 2008.
Non-Final Office Action in U.S. Appl. No. 10/433,981, all pages, mailed Jan. 19, 2005.
Non-Final Office Action in U.S. Appl. No. 10/433,981, all pages, mailed Aug. 12, 2005.
Non-Final Office Action in U.S. Appl. No. 10/433,981, all pages, mailed Mar. 13, 2006.
Final Office Action in U.S. Appl. No. 10/433,981, all pages, mailed May 16, 2007.
Non-Final Office Action in U.S. Appl. No. 10/433,981, all pages, mailed Sep. 26, 2007.
Non-Final Office Action in U.S. Appl. No. 10/433,981, all pages, mailed May 1, 2008.
Final Office Action in U.S. Appl. No. 10/433,981, all pages, mailed Jan. 13, 2009.
Non-Final Office Action in U.S. Appl. No. 10/512,135, all pages, mailed Feb. 21, 2007.
Non-Final Office Action (corrected) in U.S. Appl. No. 10/512,135, all pages, mailed Feb. 21, 2007.
Non-Final Office Action in U.S. Appl. No. 10/546,905, all pages, mailed Apr. 3, 2009.
Final Office Action in U.S. Appl. No. 10/546,905, all pages, mailed Nov. 10, 2009.

* cited by examiner

PROCESS FOR PRODUCTION OF CYCLIC POLYORGANOSILOXANE, CURING AGENT, CURABLE COMPOSITION, AND CURED PRODUCT OF THE CURABLE COMPOSITION

This application is the U.S. national phase of International Application No. PCT/JP2008/070350, filed 7 Nov. 2008, which designated the U.S. and claims priority to Japanese Patent Application No. 2007-292451, filed 9 Nov. 2007 the entire contents of each of which are hereby incorporated by reference.

TECHNICAL FIELD

The present invention relates to a curable composition and a cured product mainly for use as optical material. More specifically, the present invention relates to a cyclic polyorganosiloxane, curing agent, and curable composition, each of which has excellent heat and light resistant transparency and excellent crack resistance, and a cured product obtained by curing the same.

BACKGROUND ART

Generally, an optical semiconductor device is constructed by sealing with resin an optical semiconductor element such as a light emitting diode or a photodiode, by use of silicone resin, epoxy resin or like resin. With blue LED and white LED that have been recently given attention to, the sealing resin thus used is required to have not just optical transparency and light resistant transparency but also properties such as (i) heat resistant transparency that can resist heat generation while passing through electricity and (ii) crack resistance so that no crack generates in the sealing resin due to thermal impact upon mounting or the like.

If a conventional epoxy resin composition is used as the sealing resin, the heat and light resistance is insufficient, and brightness deteriorates in a short period of time. Accordingly, as means for improving light resistance, techniques that use an alicyclic epoxy resin as follows have been made available (e.g., Patent Literatures 6 and 7).

Chem. 9

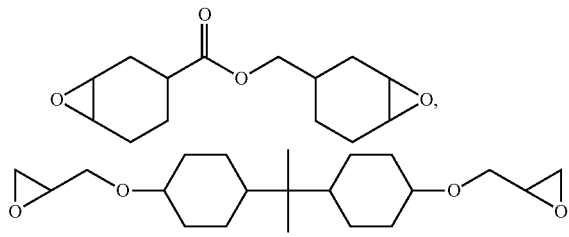

However, even with the technique that uses the alicyclic epoxy resin, the heat resistant transparency is still insufficient, and further improvement in heat resistant transparency has been strongly requested for.

Silicone resin is known as a sealing resin that has excellent heat and light resistant transparency as compared to the epoxy resin. However, although the silicone resin has excellent heat and light resistant transparency as compared to the epoxy resin, the silicone resin is weak in strength. Due to this weak resin strength, a hard silicone resin cured product easily cracks upon thermal impact testing.

In response to such a problem with the silicone resin, various curable compositions have been proposed, which include, as essential components: an organic compound that has, per molecule, at least two carbon-carbon double bonds that are reactive with an SiH group; a compound that has at least two SiH groups per molecule; and a hydrosilylation catalyst (for example, see Patent Literatures 8 and 9).

For example, in view of attaining good compatibility within the curable composition and making production of a cured product easy, Patent Literature 8 discloses a curable composition that uses a compound obtained by carrying out hydrosilylation reaction to an organic compound including at least two carbon-carbon double bonds per molecule and a cyclic polyorganosiloxane having at least three SiH groups per molecule, as the compound that includes at least two SiH groups per molecule.

Moreover, Patent Literature 9 discloses a technique which improves breakage of a molded cured product, by preparing a curable composition using, as the compound including at least two SiH groups per molecule, a compound obtained by carrying out hydrosilylation reaction to an organic compound that includes one carbon-carbon double bond per molecule and a cyclic polyorganosiloxane having at least three SiH groups per molecule.

For example, the following methods are generally known as methods for producing the cyclic polyorganosiloxane:
(a) carrying out hydrolysis and condensation to an organosilane having two hydrolysable groups that bind to silicon (e.g., Patent Literatures 1 and 2);
(b) heating a chain polyorganosiloxane in the presence of water and activated clay, to obtain a cyclic polyorganosiloxane (e.g., Patent Literature 3);
(c) heating a chain polyorganosiloxane and an acid catalyst, to obtain a cyclic polyorganosiloxane (e.g., Patent Literature 4); and
(d) heating a chain polyorganosiloxane and a neutral metal alkoxide catalyst, to obtain a cyclic polyorganosiloxane (e.g., Patent Literature 5).

CITATION LIST

Patent Literature 1

Japanese Patent Application Publication, Tokukaisho, No. 54-74900 A

Patent Literature 2

Japanese Patent Application Publication, Tokukaisho, No. 60-90220 A

Patent Literature 3

Japanese Patent Application Publication, Tokukosho, No. 54-13480 A

Patent Literature 4

Japanese Patent Application Publication, Tokukokusho, No. 55-11697 A

Patent Literature 5

Japanese Patent Application Publication, Tokukaihei, No. 11-100389 A

Patent Literature 6

Japanese Patent Application Publication, Tokukai, No. 2003-292568 A

Patent Literature 7

Japanese Patent Application Publication, Tokukai, No. 2001-19742 A

Patent Literature 8

Japanese Patent Application Publication, Tokukai, No. 2002-317048 A

Patent Literature 9

Japanese Patent Application Publication, Tokukai, No. 2003-261783 A

SUMMARY OF INVENTION

Technical Problem

The inventors of the present invention found out the two following points while studying the curable composition disclosed in Patent Literatures 8 and 9 by assuming use thereof as a sealing resin: (1) in a case where the curable composition disclosed in Patent Literature 8 is used to obtain a molded product by pouring the curable composition in a mold and heating the curable composition to cure, the obtained molded product tends to crack, and (2) in a case where the curable composition disclosed in Patent Literature 9 is used, an obtained molded product tends to have insufficient heat resistance; a crack generates in the molded product, or the resin tints upon heat resistance testing of the obtained molded product.

Accordingly, an object of the present invention is to provide a curing agent and curable composition that allows obtaining a cured product having excellent heat and light resistant transparency and excellent crack resistance, and to provide a cured product obtained by curing the same.

Solution to Problem

In view of the foregoing situation, the inventors of the present invention made continuous diligent study on a curable composition including (i) an organic compound having at least two carbon-carbon double bonds per molecule, which carbon-carbon double bonds are reactive with an SiH group, (ii) a compound having at least two SiH groups per molecule, and (iii) a hydrosilylation catalyst. As a result of the study, the inventors of the present invention arrived at attempting to use a modified polyorganosiloxane compound that has at least two SiH groups per molecule, which modified polyorganosiloxane compound is obtained by using, as the compound having at least two SiH groups per molecule, a cyclic polyorganosiloxane reduced in SiH group.

However, the known method for producing the cyclic polyorganosiloxane is simply just a common method for producing a cyclic polyorganosiloxane. No method for producing, in a selective manner and in high yield, a configuration that the inventors had arrived at, which configuration is a cyclic polyorganosiloxane reduced in SiH group, has been disclosed in any of the foregoing conventional techniques.

In response to this, the inventors of the present invention first studied various methods and production conditions and repetitively carried out experiments, to establish a method for selectively producing in high yield a cyclic polyorganosiloxane reduced in SiH group, which method is one which had not been studied before. As a result of this study, the inventors found that in a method of decomposing polyorganosiloxane by heat, a resulting yield and composition of a cyclic polyorganosiloxane obtained by decomposition caused by heat is remarkably different depending on a main chain structure of the polyorganosiloxane. Further, the inventors of the present invention figured out that by decomposing a cyclic polyorganosiloxane having a specific main chain structure by heat in the presence of a catalyst, it is possible to selectively produce in high yield a cyclic polyorganosiloxane reduced in SIR group. This thus attained the production method of the present invention.

Further, the inventors of the present invention produced, with use of the cyclic polyorganosiloxane reduced in SiH group, a modified polyorganosiloxane compound that has at least two SiH groups per molecule, and cured, a curable composition that includes this modified polyorganosiloxane compound. As a result, the inventors found that such a curable composition produces a cured product that has excellent heat and light resistant transparency and excellent crack resistance. This accomplished the curable composition and curing agent used in the curable composition, of the present invention.

Namely, the present invention is a method for producing a cyclic polyorganosiloxane including: decomposing a polyorganosiloxane by heating the polyorganosiloxane in the presence of a catalyst, the polyorganosiloxane having a main chain skeleton represented by the following general formula (I):

Chem. 10

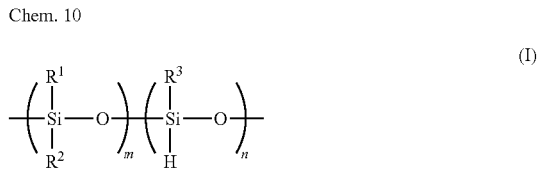

(I)

where $R^1$ to $R^3$ are identical or different monovalent substituted or unsubstituted hydrocarbon groups; and m and n satisfies: $0.3 \leq n/(m+n) < 0.9$.

The polyorganosiloxane is preferably a chain polyorganosiloxane represented by the following general formula (II):

Chem. 11

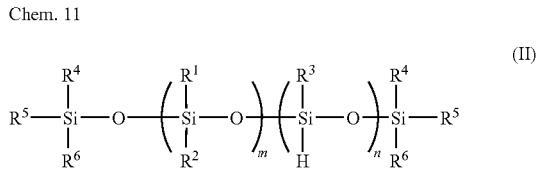

(II)

where $R^1$ to $R^3$ are identical or different monovalent substituted or unsubstituted hydrocarbon groups, $R^4$ is a monovalent substituted or unsubstituted hydrocarbon group, $R^5$ is a hydroxyl group or a monovalent substituted or unsubstituted hydrocarbon group, and $R^6$ is a hydrogen atom or a monovalent substituted or unsubstituted hydrocarbon group; m is 1 to 1000, n is 2 to 1000, the m and n satisfying: $4 < m+n < 2000$, and/or, the polyorganosiloxane is a cyclic polyorganosiloxane represented by the following general formula (III):

Chem. 12

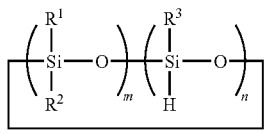
(III)

where $R^1$ to $R^3$ are identical or different monovalent substituted or unsubstituted hydrocarbon groups; m is 1 to 1000, n is 2 to 1000, the m and n satisfying: $4<m+n<2000$.

The $R^1$ to $R^3$ in the general formulae (I) to (III) are preferably a methyl group.

The catalyst is preferably a catalyst having a metal-oxygen bond, and the metal is preferably at least one selected from the group consisting of: aluminum, titanium, zirconium, tin, and zinc.

The present invention relates to a cyclic polyorganosiloxane obtained by the foregoing production method.

The cyclic polyorganosiloxane may include the following general formula (IV):

Chem. 13

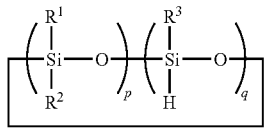
(IV)

where $R^1$ to $R^3$ are identical or different monovalent substituted or unsubstituted hydrocarbon groups; p is an integer of 1 to 8, q is an integer of 2 to 6, the p and q being integers that satisfy: $3 \leq p+q \leq 10$. The cyclic polyorganosiloxane may also include the following compounds (β1) and (β2):

Chem. 14

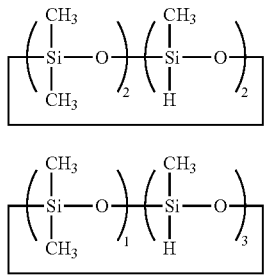
(β1)

(β2)

The present invention relates to a modified polyorganosiloxane compound having at least two SiH groups per molecule, the modified polyorganosiloxane compound being a hydrosilylation reaction product of the following compounds:
(α) an organic compound having two to six carbon-carbon double bonds per molecule, the carbon-carbon double bonds being reactive with an SiH group, and
(β) the cyclic polyorganosiloxane.

Moreover, the present invention relates to a modified polyorganosiloxane compound having at least two SiH groups per molecule, the modified polyorganosiloxane compound being a hydrosilylation reaction product of the following compounds:
(α) an organic compound having two to six carbon-carbon double bonds per molecule, the carbon-carbon double bonds being reactive with an SiH group, and
(β) a cyclic polyorganosiloxane including the following compounds (β1) and (β2):

Chem. 15

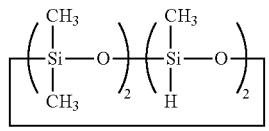
(β1)

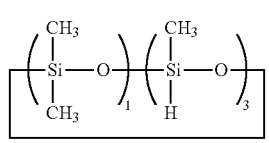
(β2)

The (β) cyclic polyorganosiloxane preferably includes the compounds (β1) and (β2) by at least 50 wt % with respect to a whole of the cyclic polyorganosiloxane.

It is preferable that the (α) organic compound is at least one cyclic organic compound selected from the group consisting of: an aromatic compound, aliphatic cyclic compound, substituted aliphatic cyclic compound and heterocyclic compound; the aromatic compound is preferably divinylbenzene, divinylnaphthalene, divinylbiphenyl, bisphenol-A diallyl ether, or bisphenol-S diallyl ether, the aliphatic cyclic compound is preferably cyclopentadiene, cyclohexadiene, cyclooctadiene, dicyclopentadiene, tricyclopentadiene, or norbornadiene, and the substituted aliphatic cyclic organic compound is preferably vinylcyclopentene, vinylcyclohexene, trivinylcyclohexane, 1,3-bis(allyloxy)adamantane, or 1,3,5-tris(allyloxy)adamantane.

The (α) organic compound preferably includes a compound represented by the following general formula (VI):

Chem. 16

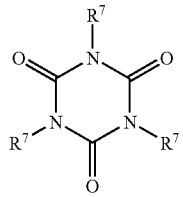
(VI)

where $R^7$ is a hydrogen atom or a monovalent organic group having a carbon number of 1 to 50, a plurality of $R^7$ being different or identical to each other; the (α) organic compound preferably includes at least one selected from the group consisting of: triallyl isocyanurate, monoglycidyl diallyl isocyanurate, and diallyl isocyanurate.

The present invention relates to a curable composition including: (A) an organic compound having at least two carbon-carbon double bonds per molecule, the carbon-carbon double bonds being reactive with a SiH group; the modified polyorganosiloxane compound of the present invention; and (C) a hydrosilylation catalyst.

The (A) organic compound is preferably at least one cyclic organic compound selected from the group consisting of: an aromatic compound, aliphatic cyclic compound, substituted aliphatic cyclic compound, and heterocyclic compound; the aromatic compound preferably is divinylbenzene, divinylnaphthalene, divinylbiphenyl, bisphenol-A diallyl ether, or bisphenol-S diallyl ether, the aliphatic cyclic compound preferably is cyclopentadiene, cyclohexadiene, cyclooctadiene, dicyclopentadiene, tricyclopentadiene, or norbornadiene, and the substituted aliphatic cyclic organic compound preferably is vinylcyclopentene, vinylcyclohexene, trivinylcyclohexane, 1,3-bis(allyloxy)adamantane, or 1,3,5-tris(allyloxy) adamantane.

The (A) organic compound preferably includes a compound represented by the following general formula (VI):

Chem. 17

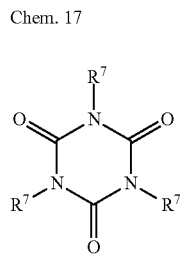

(VI)

where $R^7$ is a hydrogen atom or a monovalent organic group having a carbon number of 1 to 50, a plurality of $R^7$ being different or identical to each other.

The present invention relates to a cured product produced by curing the curable composition.

Advantageous Effects of Invention

A cured product of the present invention, of a curable composition including a modified polyorganosiloxane compound produced with use of a cyclic polyorganosiloxane reduced in SiH group, has excellent heat and light resistant transparency and excellent crack resistance. Moreover, according to a production method of the present invention, it is possible to selectively produce in high yield a cyclic polyorganosiloxane reduced in SiH group.

DESCRIPTION OF EMBODIMENTS

The following description specifically describes the present invention.

<Production Method of Cyclic Polyorganosiloxane>

First described is a method for producing a cyclic polyorganosiloxane.

A production method of the present invention is a method in which a polyorganosiloxane having a main chain skeleton represented by the general formula (I) is decomposed by heat in the presence of a catalyst.

The $R^1$ to $R^3$ in the general formula (I) are identical or different monovalent substituted or unsubstituted hydrocarbon groups, and their carbon numbers are preferably 1 to 6. Examples of the hydrocarbon group encompass: a halogenated alkyl group, alkyl group, cycloalkyl group, alkenyl group, cycloalkenyl group, and aryl group.

Among these hydrocarbon groups, it is preferable in terms of attaining excellent heat and light resistance that the $R^1$ to $R^3$ are hydrocarbon groups that have a carbon number of 1 to 6. Examples thereof encompass: a methyl group, ethyl group, propyl group, isopropyl group, n-butyl group, s-butyl group, t-butyl group, cyclohexyl group, vinyl group, and phenyl group. It is further preferably a methyl group or a phenyl group. The most preferable is a methyl group.

The $R^1$ to $R^3$ of the polyorganosiloxane represented by the general formula (I) may be identical or different to each other per repeating unit.

Examples of the main chain structure represented by the general formula (I) of the polyorganosiloxane used in the method of the present invention encompass:

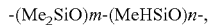
-(Me$_2$SiO)$m$-(MeHSiO)$n$-,

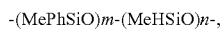
-(MePhSiO)$m$-(MeHSiO)$n$-,

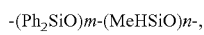
-(Ph$_2$SiO)$m$-(MeHSiO)$n$-,

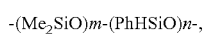
-(Me$_2$SiO)$m$-(PhHSiO)$n$-,

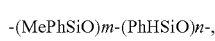
-(MePhSiO)$m$-(PhHSiO)$n$-,

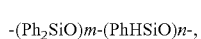
-(Ph$_2$SiO)$m$-(PhHSiO)$n$-, where Me is a methyl group, and Ph is a benzene ring.

A production method of the present invention is characterized in that it uses a polyorganosiloxane having a molar ratio of a $R^1R^2SiO$ unit and a $R^3HSiO$ unit, that is, a molar ratio in which m and n satisfy the general formula (I) of $0.3 \leq n/(m+n) < 0.9$. Note that the $R^1R^2SiO$ and $R^3HSiO$ units construct the main chain skeleton. Satisfaction of such a molar ratio allows production of a cyclic polyorganosiloxane reduced in SiH group, in high yield. In view of the yield of the cyclic polyorganosiloxane reduced in SiH group, the molar ratio is preferably $0.4 \leq n/(m+n) < 0.8$, and further preferably $0.5 \leq n/(m+n) < 0.7$. Moreover, the number of m and n in the general formula (I) is not particularly limited, however since a low viscosity attains a good workability, m is preferably 1 to 1000, n is preferably 2 to 1000, where m and n preferably satisfies $4 < m+n < 2000$. More preferably, m+n is a number from 20 to 500, and further preferably, m+n is a number from 30 to 200.

The molar ratio of the $R^1R^2SiO$ unit and the $R^3HSiO$ unit is calculated by NMR measurement.

With the method of the present invention, as long as the polyorganosiloxane has a main chain skeleton that satisfies the foregoing molar ratio, the polyorganosiloxane may be cyclic or chained. Although there is no particular limitation, in terms of availability, a chain polyorganosiloxane of the general formula (II) and/or a cyclic polyorganosiloxane of the general formula (III) is suitable.

The same details for the $R^1$ to $R^3$ in the general formula (I) applies with the R' to $R^3$ in the general formulae (II) and (III).

$R^4$ in the chain polyorganosiloxane of the general formula (II) is a monovalent substituted or unsubstituted hydrocarbon group, $R^5$ is a hydroxyl group or a monovalent substituted or unsubstituted hydrocarbon group, and $R^6$ is a hydrogen atom or a monovalent substituted or unsubstituted hydrocarbon group. Examples of the monovalent substituted or unsubstituted hydrocarbon group are as with the examples for the foregoing $R^1$. In view of availability of raw material, $R^4$ and/or $R^5$ is preferably a methyl group, and $R^6$ is preferably a hydrogen atom or a methyl group.

Examples of the chain polyorganosiloxane represented by the general formula (II) encompass:

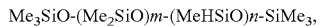
Me$_3$SiO-(Me$_2$SiO)$m$-(MeHSiO)$n$-SiMe$_3$,

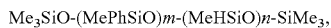
Me$_3$SiO-(MePhSiO)$m$-(MeHSiO)$n$-SiMe$_3$,

Me$_3$SiO-(Ph$_2$SiO)$m$-(MeHSiO)$n$-SiMe$_3$,

Me$_3$SiO-(Me$_2$SiO)$m$-(PhHSiO)$n$-SiMe$_3$,

Me$_3$SiO-(MePhSiO)$m$-(PhHSiO)$n$-SiMe$_3$,

Me$_3$SiO-(Ph$_2$SiO)$m$-(PhHSiO)$n$-SiMe$_3$.

Here, m is 1 to 1000, n is 2 to 1000, where m and n are numbers that satisfy: 4<m+n<2000; preferably, m n is a number in a range of 20 to 500, and further preferably m n is a number in a range of 30 to 200.

Examples of the cyclic polyorganosiloxane represented by the following general formula (III) encompass:

Chem. 18

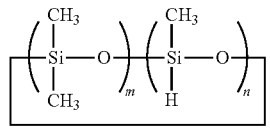

Chem. 19

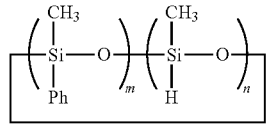

and the like. Here, m is 1 to 1000 and n is 2 to 1000, where m and n are numbers that satisfy: 4<m+n<2000; preferably, m+n is a number in a range of 20 to 500, and further preferably m+n is a number in a range of 30 to 200.

The catalyst used in the present invention may be acid, alkaline, or neutral catalysts.

Examples of methods of using an acid catalyst include (b) reacting a polysiloxane having an SiH group, in the presence of water and activated clay (Tokukokusho, No. 54-13480 A), (c) heating a methyl hydrogen polysiloxane in the presence of an acid catalyst to cause reaction thereof. (Tokukokusho, No. 55-11697 A), (e) causing an organopolysiloxane to be in contact with a heated fixed catalyst bed under reduced pressure, to cause reaction thereof (Tokukaihei, No. 2-129192 A), (f) carrying out reaction of methyl hydrogen polysiloxane in the presence of a high-boiling-point organodisiloxane (Tokukaihei, No. 7-242678), and (g) reacting organohydrogen polysiloxane in the presence of aluminum chloride (Tokukaihei, No. 7-316167). However, with the method of using the acid catalyst, since the SiH group is substantially unstable to water or the like in a system including the SiH group, for example in a case where even a least amount of moisture from raw material or from air is mixed into the system, not only that the yield of the cyclic polyorganosiloxane which is a product obtained decreases due to a reaction of the SiH group with the moisture, but also this mixture of moisture may cause gelatinization of the reaction system.

Examples of methods of using the alkaline catalyst include: (h) using a carbonate of an alkali metal as a catalyst (Tokukosho, No. 45-15036 A), and (j) using an alkali metal silanolate as a catalyst (Tokukosho, No. 33-2149). However, if the alkaline catalyst is used, procedures become complex as with the case where the acid catalyst is used, such as requiring pH adjustment at a latter step. Moreover, there also is the problem that in a system including the SiH group, the SiH group is extremely unstable under alkaline conditions.

With the production method of the present invention, a neutral catalyst is preferably used since use of a neutral catalyst causes less modification of a cyclic polyorganosiloxane product due to the minute amount of moisture as compared to a case where the acid or alkaline catalyst is used. More preferably, the catalyst includes a metal-oxygen bond. In a case where a catalyst including a metal-oxygen bond such as a metal alkoxide catalyst is used, it is advantageous in points that the catalyst has excellent storage stability, and that chlorine and moisture that may be a cause for erosion of peripheral metal components in electric material are hardly included in the cured product, thereby making it difficult for such a problem to occur when a cured product is produced.

The catalyst including the metal-oxygen bond is preferably one in which the metal is at least one selected from the group consisting of: aluminum, titanium, zirconium, tin, and zinc. Metal alkoxides are one example of the catalyst including the metal-oxygen bond, and one example is a method that uses a metal alkoxide of the following general formula (VII):

Chem. 20

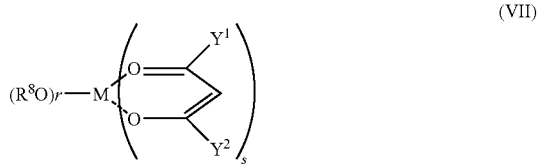

where $R^8$ is a monovalent substituted or unsubstituted hydrocarbon group, examples of the hydrocarbon group being as with $R^1$ in the general formula (I); Y1 and Y2 are alkyl groups, aryl groups, or alkoxy groups, which have a carbon number of 1 to 8; M is a bivalent to quadrivalent metal element; r and s is 0, 1, 2, 3, or 4, and r s is 2 to 4. In the method of the present invention, a metal alkoxide in which M in the general formula (VII) is Al, Ti, Zr, Sn, or Zn is preferably used, further preferably a metal alkoxide in which M is Al, Ti, or Zr is used, and most preferably aluminum alkoxide is used.

Specific examples encompass: aluminum triethoxide, aluminum triisopropoxide, aluminum tributoxide, aluminum tri-sec-butoxide, aluminum diisopropoxy-sec-butoxide, aluminum diisopropoxy acetylacetonate, aluminum di-sec-butoxy acetylacetonate, aluminum diisopropoxy ethylacetoacetate, aluminum di-sec-butoxy ethylacetoacetate, aluminum trisacetylacetonate, aluminum trisethylacetoacetate, aluminum acetylacetonate bisethylacetoacetate, titanium tetraethoxide, titanium tetraisopropoxide, titanium tetrabutoxide, titanium diisopropoxy bisacetylacetonate, titanium diisopropoxy bisethylacetoacetate, titanium tetra 2-ethylhexyl oxide, titanium diisopropoxy bis(2-ethyl-1,3-hexanediolate), titanium dibutoxy bis(triethanolaminate), zirconium tetrabutoxide, zirconium tetraisopropoxide, zirconium tetramethoxide, zirconium tributoxide monoacetylacetonate, zirconium dibutoxide bisacetylacetonate, zirconium butoxide trisacetylacetonate, zirconium tetraacetylacetonate, zirconium tributoxide monoethylacetoacetate, zirconium dibutoxide bisethylacetoacetate, zirconium butoxide trisethylacetoacetate, and zirconium tetraethylacetoacetate. Other than these, it is also possible to use cyclic 1,3,5-triisopropoxy cyclotrialuminoxane or the like. Among the above, aluminum triisopropoxide, aluminum tri-sec-butoxide, aluminum diisopropoxy ethylacetoacetate, aluminum di-sec-butoxy ethylacetoacetate, aluminum trisacetylacetonate, titanium tetraisopropoxide, titanium tetrabutoxide, or zirconium tetrabutoxide is preferably used. Most preferably used is aluminum triisopropoxide.

These metal alkoxides may be used solely, or may be used in combination in an arbitrary proportion.

Moreover, the catalyst having a metal-oxygen bond includes a catalyst having a metal-oxygen-silicon bond (Tokukai, No. 2006-273784 A) or the like.

An amount used of the catalyst in the production method of the present invention may be selected depending on a reaction speed, however it is generally preferable to use 0.01 to 10 part by weight, more preferably 0.01 to 5 parts by weight, further preferably 0.01 to 1 part by weight, each with respect to 100 parts by weight of the raw material polyorganosiloxane.

The production method of the present invention heats a polyorganosiloxane in the presence of the catalyst. A reaction temperature upon heating is sufficient as long as the reaction progresses, and generally a fluid temperature in a range of 60° C. to 300° C. is used. However, in order to prevent occurrence of side reactions while efficiently progressing in reaction, it is preferable to use a temperature in a range of 100° C. to 200° C.

The reaction in the production method of the present invention may be carried under normal or reduced pressure. However, to successively distil a formed product and efficiently progress with the reaction at a relatively low temperature, it is preferable that the reaction is carried out under reduced pressure. By carrying out the reaction in the production method of the present invention by distilling under reduced pressure, a target cyclic polyorganosiloxane is selectively produced in high yield. In this case, reaction may be carried out under a reduced pressure of 10 mmHg to 300 mmHg.

In the method of the present invention, it is possible to use an appropriate solvent if necessary. A solvent that shows no chemical reactivity against a catalyst and that has a higher boiling point than the generated cyclic polyorganosiloxane may be used as the solvent. Specific examples of the solvent encompass: decane, dodecane, mineral oil, mesitylene, diethylene glycol diethyl ether, and diethylene glycol dibutyl ether. An arbitrary amount of the solvent may be used.

With the production method of the present invention, the raw material polyorganosiloxane and the catalyst may be mixed together and heated for reaction, and a formed product may be purified by distillation after termination of the reaction. Alternatively, the formed product may be successively distilled during the reaction. In order to prevent side reactions, it is preferable to successively distill the formed product while carrying out the reaction. When the formed product is distilled, a rectifying tower such as various packed towers may be used. Use of the rectifying tower increases the purity of the product.

After the decomposition reaction, the formed product of the cyclic polyorganosiloxane obtained after carrying out the purification may be used as it is, as the (β) component of the modified polyorganosiloxane of the present invention.

The cyclic polyorganosiloxane obtained by the method of the present invention is a cyclic polyorganosiloxane reduced in SiH group, and is not particularly limited; an example of this cyclic polyorganosiloxane is a cyclic polyorganosiloxane represented by the general formula (IV).

The same applies as with $R^1$ to $R^3$ of the foregoing general formula (I), for $R^1$ to $R^3$ of the general formula (IV).

The general formula (IV) may be:

Chem. 21

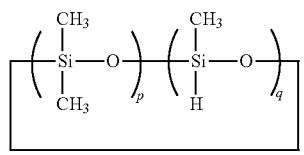

-continued
Chem. 22

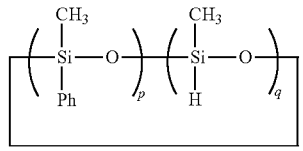

or the like. In the formula, p is an integer of 1 to 8, q is an integer of 2 to 6, which p and q are integers that satisfy: 3<p+q<10. Preferably, p is an integer of 1 to 4, q is an integer of 2 to 4, which p and q are integers that satisfy: 3<p+q<6, and further preferably p is an integer of 1 or 2, q is an integer of 2 or 3, which p and q are integers that satisfy: p+q=4.

The cyclic polyorganosiloxane obtained by the production method of the present invention may include at least one cyclic polyorganosiloxane represented by the general formula (IV).

In view of having excellent heat and light resistance, the obtained cyclic polyorganosiloxane preferably includes the general formulae (β1) and (β2).

<Curable Composition>

The curable composition of the present invention includes, as its components, (A) an organic compound having at least two carbon-carbon double bonds per molecule, which carbon-carbon double bonds are reactive with an SiH group; (B) a modified polyorganosiloxane compound; and (C) a hydrosilylation catalyst. The following description deals with each of the components.

Component (A)

The following description explains the component (A) of the present invention.

The component (A) is not particularly limited, as long as the component (A) is an organic compound including at least two carbon-carbon double bonds per molecule that is reactive with a SiH group. It is preferable that the organic compound is not one which includes a siloxane unit (Si—O—Si) as like a polysiloxane-organic block copolymer and a polysiloxane-organic graft copolymer, but is one which just includes as its constituent element an element selected from the group consisting of: C, H, N, O, S, and halogen. The organic compound including the siloxane unit causes problems in gas permeability and cissing.

A binding position of the carbon-carbon double bond that is reactive with the SiH group is not particularly limited, and the bond may exist anywhere inside the molecule.

The organic compound of the component (A) may be classified into an organic polymer-based compound and an organic monomer-based compound.

Examples of compounds that are usable as the organic polymer-based compound encompass: polyether-based, polyester-based, polyalylate-based, polycarbonate-based, saturated hydrocarbon-based, unsaturated hydrocarbon-based, polyacrylic ester-based, polyamide-based, phenol-formaldehyde-based (phenol resin-based), and polyimide-based compounds.

Moreover, examples of compounds that are usable as the organic monomer-based compound encompass: aromatic compounds such as phenol-based, bisphenol-based, benzene, and naphthalene; aliphatic compounds such as linear-based, alicyclic-based or the like; heterocyclic compounds; and mixtures thereof.

The carbon-carbon double bond of the component (A) which double bond is reactive with a SiH group is not particularly limited, however in view of reactivity, a group represented by the following general formula (VIII) is preferably used:

Chem. 23

$$CH_2=\overset{R^9}{\underset{|}{C}}-\qquad\qquad(VIII)$$

where $R^9$ is a hydrogen atom or a methyl group. Moreover, based on availability of raw material, a group represented as follows is particularly preferably used:

Chem. 24

$$CH_2=\overset{H}{\underset{|}{C}}-$$

As the carbon-carbon double bond of the component (A) which double bond is reactive with a SiH group, an alicyclic group that has a partial structure represented by the following general formula (IX) inside its ring is suitably used, in view of high heat resistance of a cured product:

Chem. 25

$$\overset{}{\underset{}{\overset{C}{\underset{\|}{C}}}}\overset{R^{10}}{\underset{R^{10}}{}}\qquad\qquad(IX)$$

where $R^{10}$ is a hydrogen atom or a methyl group. Moreover, in view of availability of raw material, an alicyclic group having a partial structure represented by the following formula inside its ring is suitably used:

Chem. 26

$$\overset{}{\underset{}{\overset{C}{\underset{\|}{C}}}}\overset{H}{\underset{H}{}}$$

The carbon-carbon double bond that is reactive with a SiH group may be directly binded to a skeleton part of the component (A), or may be covalently bonded via a bivalent or more substituent group. The bivalent or more substituent group is not particularly limited as long as it is a substituent group having a carbon number of 0 to 10, however it is preferable that just an element selected from C, H, N, O, S, and halogen is included as its structural element. Examples of the substituent group are:

Chem. 27

$$-O-,\quad -\overset{O}{\underset{\|}{C}}-,\quad -O-\overset{O}{\underset{\|}{C}}-,$$

-continued $$-O-\overset{O}{\underset{\|}{C}}-O-,\quad -\overset{O}{\underset{\|}{C}}-\overset{H}{\underset{|}{N}}-,$$

$$-O-\overset{O}{\underset{\|}{C}}-\overset{H}{\underset{|}{N}}-,\quad -S-,\quad -\overset{O}{\underset{\underset{O}{\|}}{\overset{\|}{S}}}-,$$

$$-\overset{CH_3}{\underset{|}{CH}}-,\quad -\overset{CH_3}{\underset{\underset{CH_3}{|}}{\overset{|}{C}}}-,\quad -\!\!\!\!\!\!\bigcirc\!\!\!\!\!\!-O-,$$

$$-\overset{CF_3}{\underset{\underset{CF_3}{|}}{\overset{|}{C}}}-,\quad -(CH_2)_{\overline{n}}-$$

where n is a number of 1 to 10, $$-\!\!\!\!\!\!\bigcirc\!\!\!\!\!\!-(CH_2)_{\overline{n}}-$$

where n is a number of 0 to 4, and

Chem. 28

[structure of alicyclic cage with CH, CH_2 groups, subscript n]

where n is a number of 0 to 4.

Moreover, one bivalent or more substituent group may be formed by having two or more of these bivalent or more substituent groups binded together by covalent bonding.

Examples of a group that covalently binds to a skeleton part as described above encompass: a vinyl group, allyl group, methallyl group, acrylic group, methacrylic group, 2-hydroxy-3-(allyloxy)propyl group, 2-allylphenyl group, 3-allylphenyl group, 4-allylphenyl group, 2-(allyloxy)phenyl group, 3-(allyloxy)phenyl group, 4-(allyloxy)phenyl group, 2-(allyloxy)ethyl group, 2,2-bis(allyloxymethyl)butyl group, 3-allyloxy-2,2-bis(allyloxymethyl)propyl group, and Chem. 29

$$-(CH-CH_2-O)_{\overline{n}}-CH_2-CH=CH_2$$

where n is a number that satisfies: $5 \geq n \geq n \geq 2$, $$-\!\!\!\!\!\!\bigcirc\!\!\!\!\!\!-R-\!\!\!\!\!\!\bigcirc\!\!\!\!\!\!-O-CH_2-CH=CH_2$$

where R is a bivalent group selected from:

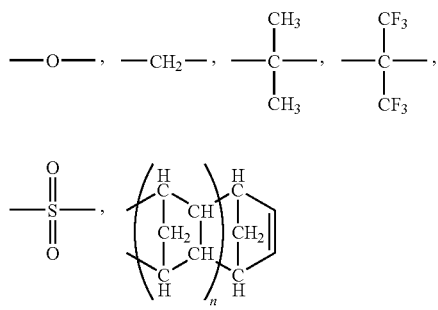

where n is a number from 0 to 4.

Specific examples of the component (A) encompass: diallyl phthalate, triallyl trimellitate, diethylene glycol bisallyl carbonate, trimethylolpropane diallyl ether, trimethylolpropane triallyl ether, pentaerythritol triallyl ether, pentaerythritol tetraallyl ether, 1,1,2,2-tetraallyloxy ethane, diallylidene pentaerythrite, triallyl cyanurate, triallyl isocyanurate, diallyl monoglycidyl isocyanurate, diallyl monobenzyl isocyanurate, 1,2,4-trivinyl cyclohexane, 1,4-butanediol divinyl ether, nonanediol divinyl ether, 1,4-cyclohexanedimethanol divinyl ether, triethylene glycol divinyl ether, trimethylolpropane trivinyl ether, pentaerythritol tetravinyl ether, bisphenol-S diallyl ether, divinylbenzene, divinyl naphthalene, divinyl biphenyl, 1,3-diisopropenyl benzene, 1,4-diisopropenyl benzene, 1,3-bis(allyloxy)adamantane, 1,3-bis(vinyloxy)adamantane, 1,3,5-tris(allyloxy)adamantane, 1,3,5-tris(vinyloxy) adamantane, dicyclopentadiene, 5-vinylbicyclo[2.2.1]hepta-2-en, vinyl cyclohexene, 1,5-hexadiene, 1,9-decadiene, diallyl ether, bisphenol-A diallyl ether, tetraallyl bisphenol-A, 2,5-diallylphenol allyl ether, and their oligomers, 1,2-polybutadiene (1,2 ratio of 10% to 100%, preferably 1,2 ratio of 50% to 100%), allyl ether of novolac phenol, the following allylated polyphenylene oxides:

Chem. 30

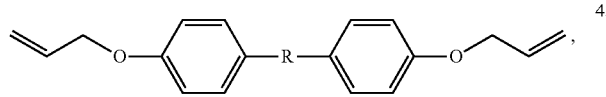

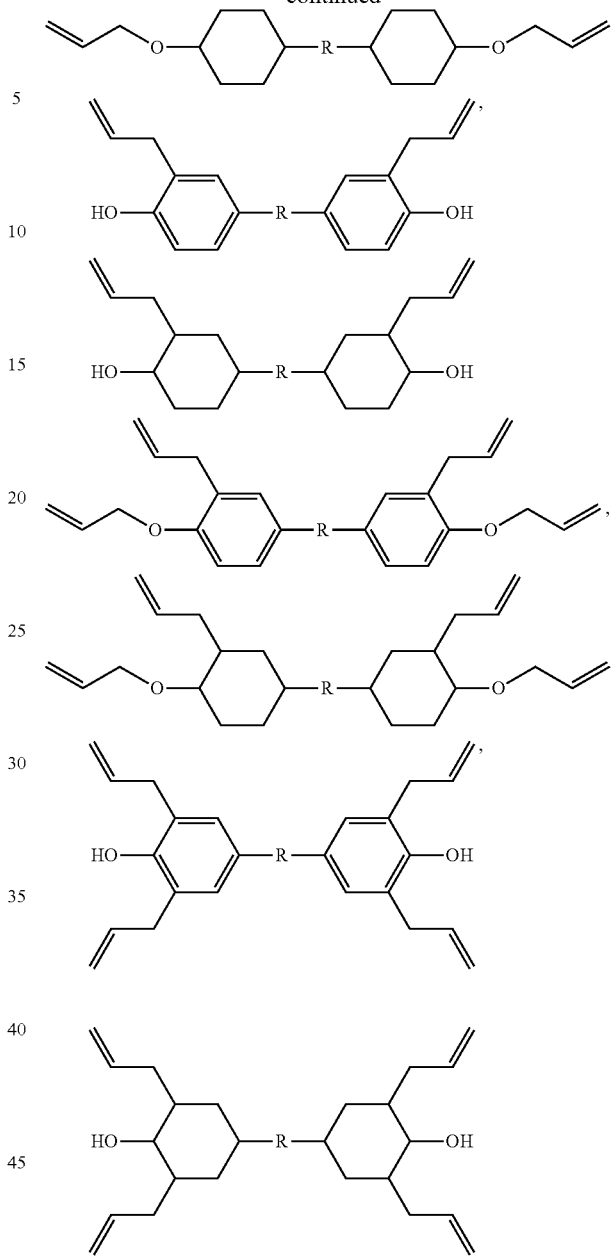

where R is a bivalent group selected from

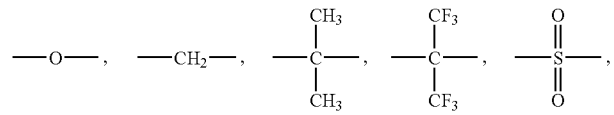

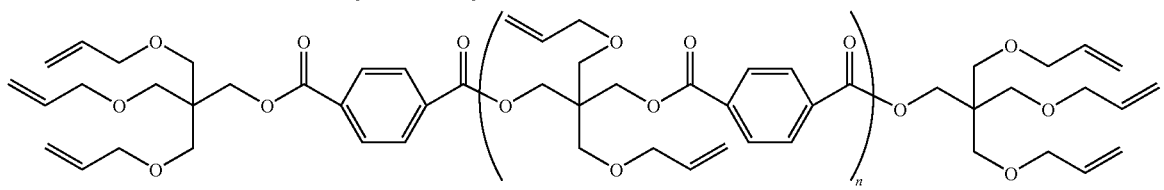

where n 1,

Chem. 31
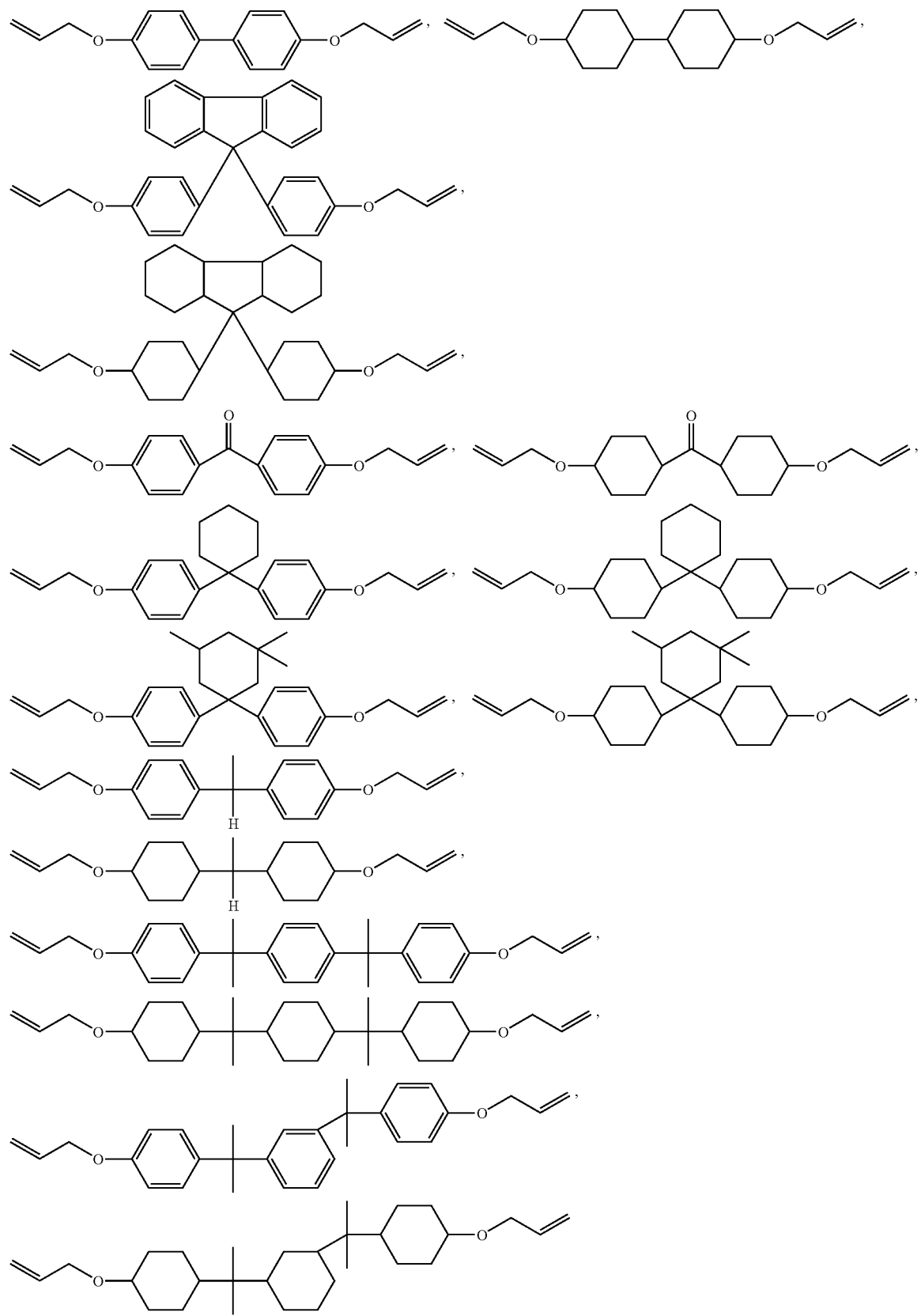

and a conventional epoxy resin in which part or all of glycidyl groups therein is substituted to an allyl group.

A low molecular weight compound may also be used as the component (A), which are difficult to separately represent the skeleton part and the alkenyl group. Specific examples of the low molecular weight compound encompass: aliphatic chain compounds such as butadiene, isoprene, octadiene, and decadiene; aliphatic cyclic compounds such as cyclopentadiene, cyclohexadiene, cyclooctadiene, dicyclopentadiene, tricyclopentadiene, and norbornadiene; and substituted aliphatic cyclic compounds such as vinylcyclopentene, and vinylcyclohexene.

In view of further improving heat resistance, the component (A) preferably includes the carbon-carbon double bond that is reactive with an SiH group, of at least 0.001 mol per 1 g of the component (A), more preferably 0.005 mol per 1 g, and further preferably 0.008 mol per 1 g.

The number of carbon-carbon double bonds included in the component (A) which double bonds react with a SiH group is sufficient if at least two is included per molecule in average. However, if the mechanical strength is to be improved, it is preferable to exceed two, and is more preferably at least three. If the included number in the component (A) of carbon-carbon double bonds that react with a SiH group is one or less per molecule, reaction with the component (B) only makes a graft structure and generates no crosslinking structure.

It is preferable that the component (A) includes at least one vinyl group per molecule, more preferably including at least two vinyl groups per molecule, since such a number attains good reactivity. Moreover, in view of attaining good storage stability, it is preferable that the component (A) includes not more than six vinyl groups per molecule, more preferably including not more than four vinyl groups.

In view of attaining (i) high mechanical heat resistance and (ii) good formability, handling, and applicability due to having low stringing properties of the raw material liquid, the component (A) preferably has a molecular weight of less than 900, more preferably less than 700, and further preferably less than 500.

In order to allow even mixing with other components and to attain good workability, the component (A) preferably has a viscosity of less than 100 Pa·s, more preferably less than 30 Pa·s, and further preferably less than 3 Pa·s, at 23° C. The viscosity is measured with an E-type viscometer.

In view of coloring, particularly prevention of yellowing, the component (A) preferably includes just a small amount of a compound including a phenolic hydroxy group and/or a derivative of a phenolic hydroxy group, and it is preferable to include no compound including a phenolic hydroxy group and/or a derivative of a phenolic hydroxy group. The phenolic hydroxy group in the present invention denotes a hydroxy group directly binded to an aromatic hydrocarbon nucleus such as a benzene ring, a naphthalene ring, or an anthracene ring, and a derivative of the phenolic hydroxy group denotes a group in which a hydrogen atom of the foregoing phenolic hydroxy group is substituted with an alkyl group such as a methyl group or an ethyl group, an alkenyl group such as a vinyl group or an allyl group, or an acyl group such as acetoxy group or the like.

In view of excellent heat and light resistance, it is preferable that the component (A) is a cyclic organic compound. More specifically, the component (A) is as follows.

In view of having less coloring and attaining high light resistance in an obtained cured product, the component (A) is preferably a cyclic organic compound such as: an aliphatic cyclic compound for example cyclopentadiene, cyclohexadiene, cyclooctadiene, dicyclopentadiene, tricyclopentadiene, or norbornadiene; a substituted aliphatic cyclic compound for example vinylcyclopentene, vinylcyclohexene, trivinylcyclohexane, 1,3-bis(allyloxy) adamantane, or 1,3,5-tris(allyloxy)adamantane; and a heterocyclic compound for example triallyl isocyanurate or diallyl monoglycidyl isocyanurate.

In view of having less coloring and attaining high heat resistance in an obtained cured product, the component (A) is preferably a cyclic organic compound such as: an aromatic compound for example divinylbenzene, divinylnaphthalene, divinylbiphenyl, bisphenol-A diallyl ether, or bisphenol-S diallyl ether; an aliphatic cyclic compound for example cyclopentadiene, cyclohexadiene, cyclooctadiene, dicyclopentadiene, tricyclopentadiene, or norbornadiene; a substituted aliphatic cyclic compound such as vinylcyclopentene, vinylcyclohexene, trivinylcyclohexane, 1,3-bis(allyloxy) adamantane, or 1,3,5-tris(allyloxy)adamantane; and a heterocyclic compound such as triallyl isocyanurate, or diallyl monoglycidyl isocyanurate.

The component (A) may have other reactive groups. Examples of the reactive groups in this case are: an epoxy group, amino group, radically polymerizable unsaturated group, carboxyl group, isocyanate group, hydroxyl group, and alkoxysilyl group. In a case where the component (A) has these functional groups, adhesivity of an obtained curable composition is likely to be strong, and the strength of an obtained cured product likely improves. In view of improvement in adhesivity, the epoxy group is preferable among these functional groups. Moreover, in view of improving heat resistance of the obtained cured product, it is preferable that at least one reactive group in average is included per molecule.

Particularly, in view of high heat and light resistance, the component (A) is preferably a compound represented by the following general formula (VI):

Chem. 32

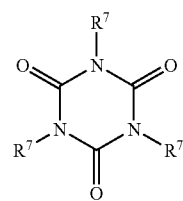

(VI)

where $R^7$ is a hydrogen atom or a monovalent organic group having a carbon number of 1 to 50, and each of $R^7$ may be different or identical to each other.

The organic group of $R^7$ in the general formula (VI), in view of high heat and light resistance, is preferably a hydrocarbon group in which one part may be substituted.

In view of high heat resistance of the obtained cured product, the $R^7$ in the general formula (VI) preferably has a carbon number of 1 to 20, more preferably a carbon number of 1 to 10, and further preferably a carbon number of 1 to 6. Examples of the preferable $R^7$ encompass: a methyl group, ethyl group, propyl group, butyl group, phenyl group, benzyl group, phenethyl group, vinyl group, allyl group, glycidyl group, Chem. 33

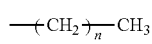

where n is a number of 4 to 19,

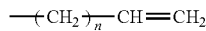

where n is a number of 2 to 18,

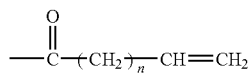

where n is a number of 0 to 17,

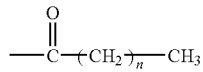

where n is a number of 0 to 18,

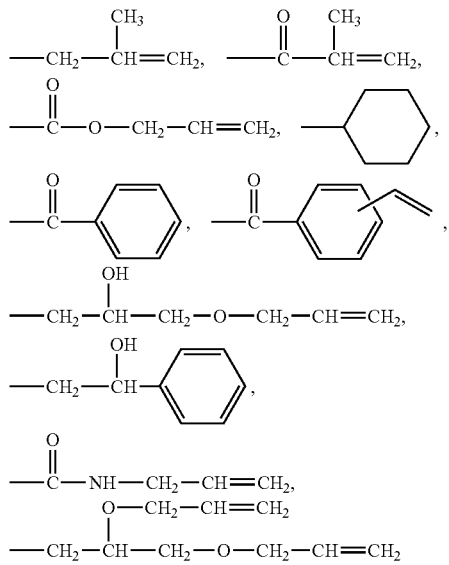

and the like.

In view of good adhesivity between various materials of the obtained cured product, as the $R^7$ in the general formula (VI), at least one of the three $R^7$s is a monovalent organic group having a carbon number of 1 to 50 and including at least one epoxy group, and is further preferably a monovalent organic group having a carbon number of 1 to 50 and that includes an epoxy group represented by the following general formula:

Chem. 34

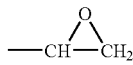

Examples of the preferable $R^7$ encompass: a glycidyl group,

Chem. 35

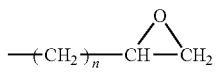

where n is a number of 2 to 18,

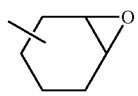

or the like.

In view of attaining good chemical thermal stability of the cured product, the $R^7$ in the general formula (VI) is preferably a monovalent organic group having a carbon number of 1 to 50 and that includes two or less oxygen atoms and includes just an element selected from C, H and O as its structural element, and is more preferably a monovalent hydrocarbon group having a carbon number of 1 to 50. Preferable examples of the $R^7$ encompass: a methyl group, ethyl group, propyl group, butyl group, phenyl group, benzyl group, phenethyl group, vinyl group, allyl group, glycidyl group, Chem. 36

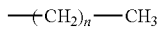

where n is a number of 4 to 49,

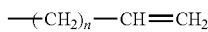

where n is a number of 2 to 48,

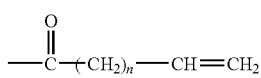

where n is a number of 0 to 47,

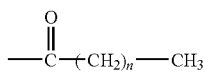

where n is a number of 0 to 48,

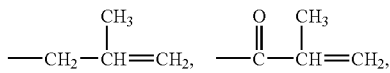

-continued

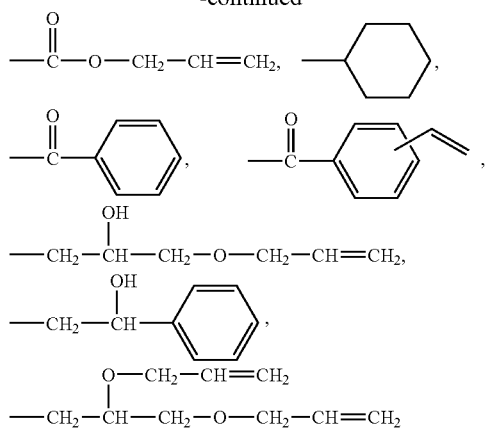

and the like.

In view of good reactivity, as the $R^7$ in the following formula (VI), at least one of the three $R^7$s is preferably a monovalent organic group having a carbon number of 1 to 50 and including at least one group represented by the following:

Chem. 37

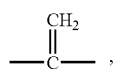

is more preferably a monovalent organic group having a carbon number of 1 to 50 and including at least one group represented by the following general formula (VIII):

Chem. 38

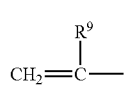 (VIII)

where $R^9$ is a hydrogen atom or a methyl group, and is further preferably an organic compound in which at least two of the three $R^7$s are each a group represented by the following general formula (X):

Chem. 39

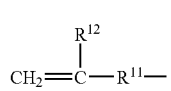 (X)

where $R^{11}$ is a directly bonded organic group or a bivalent organic group having a carbon number of 1 to 48, and $R^{12}$ is a hydrogen atom or a methyl group. Note that each of the $R^{11}$ and $R^{12}$ may be different or identical to each other.

$R^{11}$ in the general formula (X) is a directly bonded organic group or a bivalent organic group having a carbon number of 1 to 48, however in view of attaining further high heat resistance of the obtained cured product, it is preferably a directly bonded organic group or a bivalent organic group having a carbon number of 1 to 20, is more preferably a directly bonded organic group or a bivalent organic group having a carbon number of 1 to 10, and is further preferably a directly bonded organic group or a bivalent organic group having a carbon number of 1 to 4. Examples of the preferable $R^{11}$ encompass:

Chem. 40

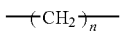

where n is a number of 1 to 17,

where n is a number of 0 to 16,

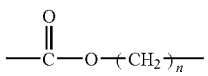

where n is a number of 0 to 16,

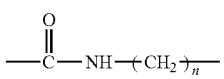

where n is a number of 0 to 16,

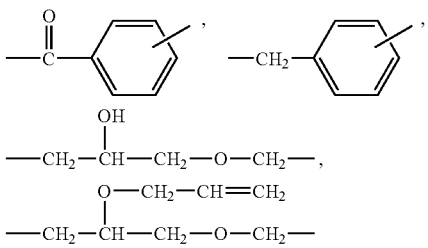

and the like.

In view of attaining good chemical thermal stability of the attained cured product, the $R^{11}$ of the general formula (X) is preferably a directly bonded organic group or an organic group having a carbon number of 1 to 48 and including two or less oxygen atoms and just an element selected from C, H and O as a constituent element, and is more preferably a directly bonded hydrocarbon group or a bivalent hydrocarbon group having a carbon number of 1 to 48. Preferable examples of the $R^{11}$ encompass:

Chem. 41

where n is a number of 1 to 47,

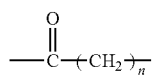

where n is a number of 0 to 46,

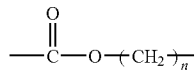

where n is a number of 0 to 46,

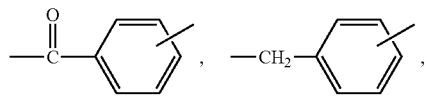

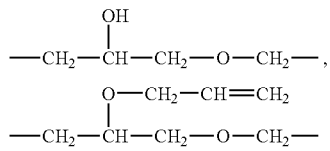

and the like.

The $R^{12}$ in the general formula (X) is a hydrogen atom or a methyl group. In view of good reactivity, $R^{i2}$ is preferably a hydrogen atom.

However, in a preferable example of the organic compound represented by the foregoing general formula (VI), it is necessary to include at least two carbon-carbon double bonds that are reactive with a SiH group. In view of further improving heat resistance, it is preferable that the organic compound is an organic compound that includes at least three carbon-carbon double bonds that are reactive with a SiH group.

Specific preferable examples of the organic compounds represented by the general formula (VI) encompass: triallyl isocyanurate, diallyl isocyanurate, Chem. 42

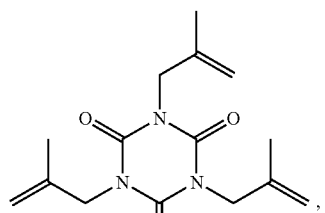

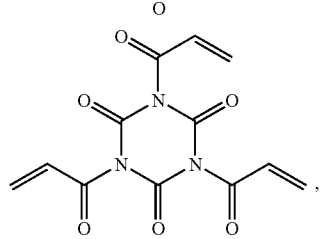

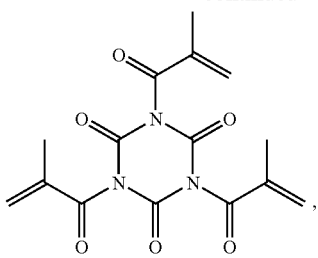

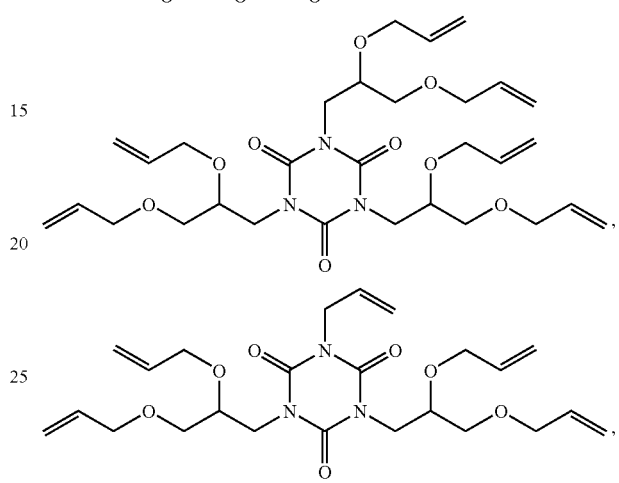

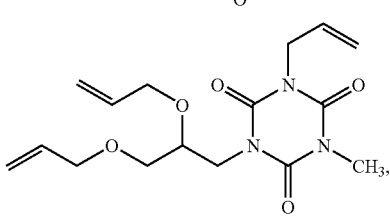

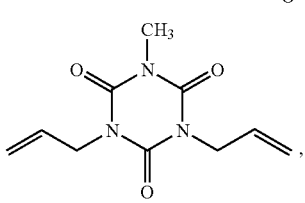

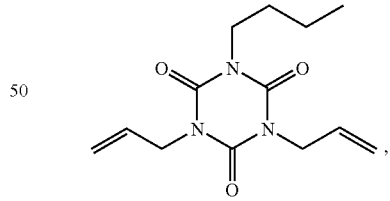

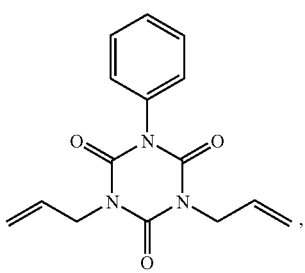

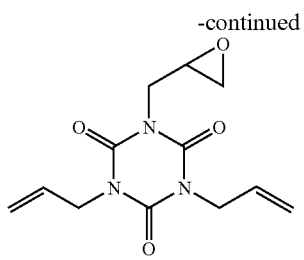

and the like.

In order to improve adhesivity of the cured product, the component (A) is preferably diallyl monoglycidyl isocyanurate.

To attain both of improvement in adhesitivity and light resistance with the cured product, it is preferable that the component (A) is a mixture of triallyl isocyanurate and diallyl monoglycidyl isocyanurate. The mixture is effective also from the point of heat resistance, since the mixture has an isocyanuric ring skeleton. A mixed ratio may be arbitrary set, however in order to attain the object, it is preferable that triallyl isocyanurate/diallyl monoglycidyl isocyanurate (molar ratio) is 9/1 to 1/9, further preferably is 8/2 to 2/8, and most preferably is 7/3 to 3/7.

The component (A) may be used solely, or two or more types thereof may be used in combination.

Component (B)

The following description explains component (B).

The curable composition of the present invention is characterized in that, as the component (B), a modified polyorganosiloxane compound having at least two SiH groups per molecule is used, which modified polyorganosiloxane compound is a hydrosilylation reaction product of the following compounds (α) and (β):

(α) an organic compound having two to six carbon-carbon double bonds per molecule, which double bonds are reactive with an SiH group; and (β) a cyclic polyorganosiloxane obtained by the foregoing method of the present invention, or a cyclic polyorganosiloxane including general formulae (β1) and (β2).

The component (β) may be used as the component (B) as it is to form the curable composition, however if the component (β) is volatile, the component (β) may volatilize while curing. Moreover, since the component (β) is a siloxane component, the compatibility with the organic compound of the component (A) is poor. This often becomes a cause for problems in compatibility within the curable composition. By using the component (β) as the modified polyorganosiloxane compound, these problems are improved.

Various methods for synthesizing the component (β) are available, however the most simple synthesizing method to obtain the component (B) is to react, under the presence of a hydrosilylation catalyst, (i) the cyclic polyorganosiloxane (β) and (ii) the organic compound (α) that includes two to six carbon-carbon double bonds per molecule which double bonds are reactive with an SiH group, and thereafter remove the component (β) that did not react.

Component (α)

As the organic compound having two to six carbon-carbon double bonds per component (α) molecule, which double bonds are reactive with a SiH group, an organic compound that has two to six carbon-carbon double bonds that are reactive with a SiH group is usable among the components (A), and compounds that are suitable as the component (A) may also be similarly used as the component (α).

In view of good availability and good workability, the component (α) preferably is an organic compound that has two to four carbon-carbon double bonds per molecule which double bonds are reactive with a SiH group, and that has a molecular weight of less than 900.

The compound (α), in view of heat and light resistance, is preferably a cyclic organic compound.

It is preferable that at least one selected from the group consisting of: an aromatic compound, aliphatic cyclic compound, substituted aliphatic cyclic compound, and heterocyclic compound is used as the cyclic organic compound. More specifically, preferable compounds encompass: aromatic compounds such as divinylbenzene, divinylnaphthalene, divinylbiphenyl, bisphenol-A diallyl ether, and bisphenol-S diallyl ether; aliphatic cyclic compounds such as cyclopentadiene, cyclohexadiene, cyclooctadiene, dicyclopentadiene, tricyclopentadiene, and norbornadiene; substituted aliphatic cyclic compounds such as vinylcyclopentene, vinylcyclohexene, trivinyicyclohexane, 1,3-bis(allyloxy)adamantane and 1,3,5-tris(allyloxy)adamantane; and heterocyclic compounds such as triallyl isocyanurate, and diallyl monoglycidyl isocyanurate.

In view of attaining a cured product having good heat and light resistant transparency, the component (α) is preferably an organic compound represented by the following general formula (VI):

Chem. 43

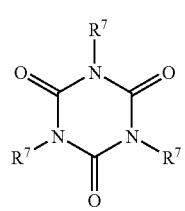

(VI)

where $R^7$ is a hydrogen atom or a monovalent organic group having a carbon number of 1 to 50, and each of the $R^7$ may be different or identical to each other. Among the organic compounds, triallyl isocyanurate, diallyl monoglycidyl isocyanurate, or diallyl isocyanurate is more preferable in view of good availability and good heat and light resistance of a cured product.

Component (β)

A cyclic polyorganosiloxane usable as the cyclic polyorganosiloxane of the component (β) in the present invention is a cyclic polyorganosiloxane obtained by the foregoing method of producing a cyclic polyorganosiloxane, more specifically a cyclic polyorganosiloxane including the following general formula (IV):

Chem. 44

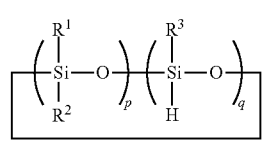

(IV)

where $R^1$ to $R^3$ are identical or different monovalent substituted or unsubstituted hydrocarbon groups; p is an integer of 1 to 8, q is an integer of 2 to 6, which p and q are integers that satisfy: $3 \leq p+q \leq 10$; the p and q being identical or different per repetitive unit.

The $R^1$ to $R^3$ in the following formula (IV) are identical or different monovalent substituted or unsubstituted hydrocarbon groups, and examples of the hydrocarbon group encompass: a halogenated alkyl group, alkyl group, cycloalkyl group, alkenyl group, cycloalkenyl group, and aryl group.

Among these hydrocarbon groups, the methyl group and phenyl group are preferable in view of good availability.

Moreover, the phenyl group is preferable in view of high resin strength of the cured product.

Moreover, the methyl group is preferable in view of high heat and light resistant transparency of the cured product.

In view of easy isolation by distillation purification, p+q preferably satisfies $3 \leq p+q \leq 6$, and further preferably satisfies an equation of p+q=4.

In view of improving crack resistance of a cured product, q preferably satisfies $3 \leq p+q \leq 6$ and is an integer of 2 to 4, and further preferably q satisfies an equation of p+q=4 and is an integer of 2 or 3.

A specific example of the component (β) encompass:

Chem. 45

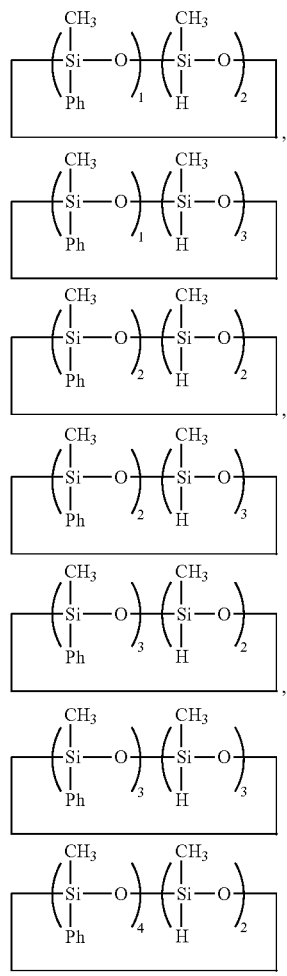

Chem. 46

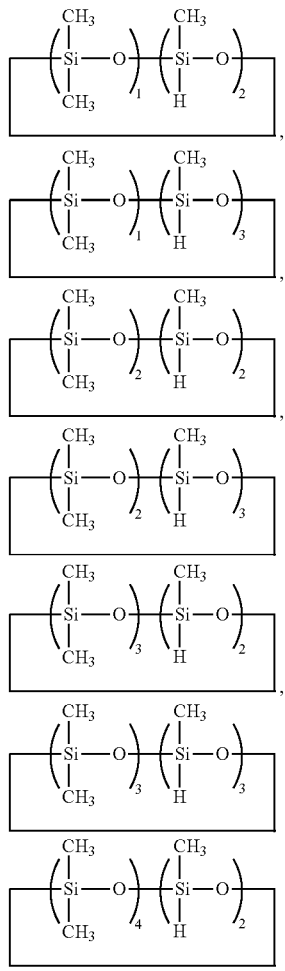

and the like. The p and q may be identical or different per repeating unit.

Among these components (β), in view of heat and light resistance, it is preferable to use a cyclic polyorganosiloxane including (β1) and (β2). The cyclic polyorganosiloxane including (β1) and (β2) may be one in which (β1) and (β2) are mixed together, however since the method of the present invention can efficiently obtain a mixture of (β1) and (β2), the cyclic polyorganosiloxane obtained by the present invention may be used as it is.

Content of (β1) and (β2) of the cyclic polyorganosiloxane of the present invention is preferably at least 50% by weight, more preferably at least 65% by weight, and further preferably at least 80% by weight, in view of easily expressing object heat and light resistant transparency and crack resistance since the amount of side effects caused is small when producing the modified polyorganosiloxane compound (B) using the compound (β) and thereafter producing a cured product using the compound (B).

A cyclic and/or chain polyorganosiloxane compound of a low molecular weight not including the SiH group, which has the possibility of being mixed into the cyclic polyorganosiloxane of the present invention during a manufacturing step, has no hydrosilylation reactivity. Thus, this can be used as a solvent. Therefore, the cyclic and/or chain polyorganosiloxane of a low molecular weight not including a SiH group may be removed after hydrosilylation reaction of the component (α) and the component (β) by volatilization or the like.

As long as a curing physical property is not lost, it is possible to use a different compound having a SiH group other than the component (β) in the modified polyorganosiloxane. The compound having a SiH group may be, for example, a compound disclosed in International Patent Application Publication No. WO 96/15194, in which at least three SiH groups are included per molecule.

A ratio of the components in a case where the component (α) and component (β) are hydrosilylation reacted is not particularly limited as long as handling property of the component (B) is not lost. However, it is preferable that a ratio (Y/X) has a lower limit of 1.5, more preferably 3, and has an upper limit of 10, more preferably 6, where (Y) is the number of SiH groups in the component (β) and (X) is the number of carbon-carbon double bonds in the component (α). If Y/X is a smaller value than 1.5, viscosity of the component (B) increases, thereby losing its handling property. This causes a possibility of the component (B) to gelatinize. On the other hand, if the Y/X is a value greater than 10, the amount of the unreacted component (β) remaining after the hydrosilylation reaction increases, thereby increasing manufacturing costs of the component (B).

The following examples may be used as a catalyst in a case where the component (α) and the component (β) are hydrosilylation reacted: simple platinum; a carrier made of alumina, silica, carbon black or the like with which solid platinum is carried and supported; chloroplatinic acid; a complex of chloroplatinic acid and alcohol, aldehyde, ketone or the like; platinum-olefin complex (e.g., $Pt(CH_2=CH_2)_2(PPh_3)_2$, $Pt(CH_2=CH_2)_2Cl_2$); platinum-vinyl siloxane complex (e.g, $Pt(ViMe_2SiOSiMe_2Vi)_n$, $Pt[(MeViSiO)_4]_m$); platinum-phosphine complex (e.g., $Pt(PPh_3)_4$, $Pt(PBu_3)_4$); platinum phosphite complex (e.g., $Pt[P(OPh)_3]_4$, $Pt[P(OBu)_3]_4$)(where Me denotes a methyl group, Bu denotes a butyl group, Vi denotes a vinyl group, and Ph denotes a phenyl group, and n and m are integers); dicarbonyl dichloroplatinum, Karstedt catalyst, and also a platinum-hydrocarbon complex disclosed in specifications of U.S. Pat. No. 3,159,601 and No. 3159662 of Ashby and a platinum alcoholate catalyst disclosed in a specification of U.S. Pat. No. 3,220,972 of Lamoreaux. Furthermore, a chloroplatinum-olefin complex disclosed in U.S. Pat. No. 3,516,946 of Modic is also usable in the present invention.

Moreover, examples of catalysts other than platinum compounds encompass: $RhCl(PPh)_3$, $RhCl_3$, $RhAl_2O_3$, $RuCl_3$, $IrCl_3$, $FeCl_3$, $AlCl_3$, $PdCl_2 \cdot 2H_2O$, $NiCl_2$, and $TiCl_4$.

Among these catalysts, the chloroplatinic acid, platinum-olefin complex, platinum-vinyl siloxane complex or the like is preferable in view of catalyst activation. Moreover, these catalysts may be used solely, or two or more types thereof may be used in combination.

The catalyst is not limited in how much amount is added, however in view of adding platinum atoms to attain sufficient hydrosilylation reactivity, the amount of platinum atom (mole number)/carbon-carbon double bond group (mole number) of component (α) is preferably $10^{-2}$ to $10^{-8}$, more preferably $10^{-4}$ to $10^{-6}$.

Moreover, the catalyst may be used together with a catalytic promoter, and examples thereof encompass: phosphorus compounds such as triphenylphosphine, 1,2-diesteric compounds such as dimethylmalate, acetylene alcoholic compounds such as 2-hydroxy-2-methyl-1-butine and 1-ethynyl-1-cyclohexanol, and sulfuric compounds such as simple sulfur. An amount of the catalytic promoter to be added is not particularly limited, however a preferable lower limit of the added amount with respect to one mole of hydrosilylation catalyst is $10^{-2}$ mol, more preferably $10^{-1}$ mol, and a preferable upper limit of the added amount is $10^2$ mol, more preferably 10 mol.

Various methods may be used to mix the component (α), component (β), and catalyst together in a case where these are to be reacted, however it is preferable to mix the component (β) with a mixture of the component (α) and the catalyst. If the catalyst is mixed with a mixture of the components (α) and (β), it is difficult to control the reaction. A method in which the component (α) is mixed with a mixture of the component (β) and the catalyst may cause a change in state, since the component (β) in the presence of the catalyst is reactive with moisture.

A reaction temperature may be set variously, however a lower limit of a preferable temperature range is 30° C., more preferably 50° C., and an upper limit of a preferable temperature range is 200° C., more preferably 150° C. A low reaction temperature requires a long reaction time in order to sufficiently carry out reaction, and a high reaction temperature is not practical. The reaction may be carried out at a fixed temperature, however the temperature may be changed in multiple stages or in a successive manner, if necessary.

A reaction time and pressure upon reaction may be set variously if necessary.

A solvent may be used upon hydrosilylation reaction. A solvent that may be used is not particularly limited as long as the solvent does not disturb the hydrosilylation reaction, and specific examples encompass: hydrocarbon-based solvents such as benzene, toluene, hexane, and heptane; ether-based solvents such as tetrahydrofuran, 1,4-dioxane, 1,3-dioxolane, and diethyl ether; ketone-based solvents such as acetone and methyl ethyl ketone; and halogen-based solvents such as chloroform, methylene chloride, and 1,2-dichloroethane. The solvent may be used as a mixed solvent of two or more types. Toluene, tetrahydrofuran, 1,3-dioxolane, or chloroform is preferably used as the solvent. The amount of solvent used may be set as appropriate.

Other than the foregoing, various additives may be used for controlling reactive properties and the like.

The solvent and/or component (β) not reacted and/or component (α) may be removed after the components (α) and (β) are reacted. By removing these volatilizing parts, the component (B) thus obtained will not include the volatilizing parts, thereby reducing the possibility of void and crack generation upon curing with the component (A), which void and crack generation is caused by the volatilizing components. Removal may be carried out, other than the volatilization under pressure, by processing with active carbon, aluminum silicate, silica gel or the like. In a case where the volatilization under pressure is carried out, the process is preferably carried out at a low temperate. A preferable upper limit temperature in this case is 100° C., and more preferably is 80° C. Carrying out this process at a high temperature may cause deterioration in viscosity or the like.

Reactant examples of the component (α) and (β) included in the component (B) as like the above encompass: a reactant of triallyl isocyanurate and the component (β1 and/or β2); a reactant of diallyl monoglycidyl isocyanurate and the component (β1 and/or β2); a reactant of diallyl isocyanurate and the component (β1 and/or β2); a reactant of trimethylolpropane diallyl ether and the component (β1 and/or β2); a reactant of trimethylolpropane triallyl ether and the component (β1 and/or β2); a reactant of pentaerythritol triallyl ether and the component (β1 and/or β2); a reactant of pentaerythritol tetraallyl ether and the component (β1 and/or β2); a reactant of 1,1,2,2-tetraallyloxyethane and the component (β1 and/or β2); a reactant of 1,5-hexadiene and the component (β1 and/or β2); a reactant of 1,9-decadiene and the component (β1 and/or β2); a reactant of diallyl ether and the component (β1 and/or β2); a reactant of divinylbenzene and the component (β1 and/or β2); a reactant of divinylnaphthalene and the component (β1 and/or β2); a reactant of divinylbiphenyl and the component (β1 and/or β2); a reactant of bisphenol-S diallyl ether and the component (β1 and/or β2; a reactant of bisphenol-A diallyl ether and the component (β1 and/or β2); a reactant of tetraallyl bisphenol-A and the component (β1 and/or β2); a reactant of cyclopentadiene and the component (β1 and/or β2); a reactant of cyclohexadiene and the component (β1 and/or β2); a reactant of cyclooctadiene and the component (β1 and/or β2); a reactant of dicyclopentadiene and the component (β1 and/or β2); a reactant of tricyclopentadiene and the component (β1 and/or β2); a reactant of norbornadiene and the component (β1 and/or β2); a reactant of 1,2,4-trivinylcyclohexane and the component (β1 and/or β2); a reactant of vinylcyclopentene and the component (β1 and/or β2); a reactant of vinylcyclohexene and the component (β1 and/or β2); a reactant of 1,4-cyclohexanedimethanol divinyl ether and the component (β1 and/or β2); a reactant of 1,3-bis(allyloxy)adamantane and the component (β1 and/or β2), a reactant of 1,3-bis(vinyloxy)adamantane and the component (β1 and/or β2); a reactant of 1,3,5-tris(allyloxy)adamantane and the component (β1 and/or β2); and a reactant of 1,3,5-tris(vinyloxy)adamantae and the component (β1 and/or β2).

In view of heat and light resistance and adhesitivity of a cured product, it is preferable to include the reactant of triallyl isocyanurate and the component (β1 and/or β2), the reactant of diallyl monoglycidyl isocyanurate and the component (β1 and/or β2), or the reactant of diallyl isocyanurate and the component (β1 and/or β2).

In view of handling and processing properties of the component (B), a viscosity is preferably not more than 1000 Pa·s, is more preferably not more than 100 Pa·s, and is further preferably not more than 10 Pa·s, at 23° C.

The component (B) may be used solely, or two or more types thereof may be used in combination.

Mixed Ratio of Components (A) and (B)

A mixed ratio of the components (A) and (B) is not particularly limited as long as a strength required for the cured product is not lost, however a ratio (Y'/X') preferably has a range in which a lower limit is 0.3, more preferably 0.5, further preferably 0.7, and an upper limit is 3, more preferably 2, further preferably 1.5, where Y' is a number of SiH groups in the component (B) and X' is the number of carbon-carbon double bonds in the component (A). If the ratio is not within the preferable range, the strength obtained may be insufficient, or the cured product may deteriorate due to heat.

Component (C)

The following description deals with the component (C), which is a hydrosilylation catalyst.

The hydrosilylation catalyst is not particularly limited as long as it has catalyst activity of a hydrosilylation reaction, and examples thereof encompass: simple platinum; a carrier made of alumina, silica, carbon black or the like with which solid platinum is supported; chloroplatinic acid; a complex of chloroplatinic acid and alcohol, aldehyde, ketone or the like; platinum-olefin complex (e.g., $Pt(CH_2=CH_2)_2(PPh_3)_2$, $Pt(CH_2=CH_2)_2Cl_2$); platinum-vinyl siloxane complex (e.g, $Pt(ViMe_2SiOSiMe_2Vi)_n$, $Pt[(MeViSiO)_4]_m$); platinum-phosphine complex (e.g., $Pt(PPh_3)_4$, $Pt(PBu_3)_4$); platinum-phosphite complex (e.g., $Pt[P(OPh)_3]_4$, $Pt[P(OBu)_3]_4$) (where Me denotes a methyl group, Bu denotes a butyl group, Vi denotes a vinyl group, and Ph denotes a phenyl group, and n and m are integers); dicarbonyl dichloroplatinum, Karstedt catalyst, and also a platinum-hydrocarbon complex disclosed in the specification of U.S. Pat. No. 3,159,601 and No. 3159662 of Ashby and a platinum alcoholate catalyst disclosed in the specification of U.S. Pat. No. 3,220,972 of Lamoreaux.

Furthermore, a chloroplatinum-olefin complex disclosed in U.S. Pat. No. 3,516,946 of Modic is also usable in the present invention.

Moreover, examples of catalysts other than platinum compounds encompass $RhCl(PPh_3)_3$, $RhCl_3$, $RhAl_2O_3$, $RuCl_3$, $IrCl_3$, $FeCl_3$, $AlCl_3$, $PdCl_2.2H_2O$, $NiCl_2$, and $TiCl_4$.

Among these catalysts, the chloroplatinic acid, platinum-olefin complex, platinum-vinyl siloxane complex or the like is preferable, in view of catalyst activity. Moreover, these catalysts may be used solely, or two or more types thereof may be used in combination.

The catalyst is not particularly limited in an added amount, however in order to attain a sufficient curability and to relatively reduce costs of the curable composition, a preferable lower limit of the added amount is $10^{-8}$ mol, more preferably $10^{-6}$ mol with respect to 1 mol of a SiH group in the component (B), and a preferable upper limit of the added amount is $10^{-1}$ mol, more preferably $10^{-2}$ mol with respect to 1 mol of the SiH group in the component (B).

Moreover, it is possible to simultaneously use a catalytic promoter together with the catalyst, and examples thereof encompass: phosphorus compounds such as triphenylphosphine, 1,2-diesteric compounds such as dimethylmalate, acetylene alcoholic compounds such as 2-hydroxy-2-methyl-1-butine, and sulfuric compounds such as simple sulfur. The amount of the catalytic promoter to be added is not particularly limited, however a preferable lower limit of the added amount with respect to one mole of hydrosilylation catalyst is $10^{-2}$ mol, more preferably $10^{-1}$ mol, and a preferable upper limit of the added amount is $10^2$ mol, more preferably 10 mol.

In a case where a hydrosilylation catalyst is used upon synthesis of the component (B), and the component (B) is used without removing the hydrosilylation catalyst, the hydrosilylation catalyst remaining in the component (B) is also included as the component (C) of the present invention.

Method for Preparing and Curing Curable Composition

How the curable composition is prepared is not particularly limited, and may be prepared by various methods. Various components may be mixed and prepared immediately before curing, or all the components may be mixed into one liquid in advance and be stored at a low temperature. Alternatively, to prepare the composition, the components may be partially mixed in advance so that two or three types of mixtures are prepared beforehand and stored, and thereafter mixing these mixtures together in predetermined amounts immediately before curing. It is preferable to separately store the component (A) and the component (B) since the physical property during storage least deteriorates.

A mixing order of the components is also not particularly limited, however it is preferable that a mixed liquid of the components (A) and (C) and the component (B) are stored separately, and the mixed liquid of the components (A) and (C) and the component (B) are mixed and stirred together before curing, to cure the composition. It is difficult to control reaction with a method in which a mixed liquid of the component (A) and component (B) is mixed, with the component (C). A method in which the component (A) is mixed with a mixed liquid of the components (B) and (C) may cause change in state during storage, since the component (B) is reactive with moisture in the environment.

Moreover, the following method may also be taken: (i) the functional groups in the composition is just partially reacted (B-staged) by controlling reaction conditions and utilizing a difference in reactivity of substituent groups, (ii) formation process or the like is carried out, then (iii) the formed product is cured. These foregoing methods make it easy to adjust viscosity at the time of formation.

As the curing method, reaction may be caused just by simply mixing the composition, or the reaction may be caused by applying heat. In view that the reaction is carried out quickly and generally material with high heat resistance is obtainable, it is preferable to cause reaction by applying heat.

Various settings are possible as the curing temperature, however a lower limit of a preferable temperature is 30° C., more preferably 100° C. An upper limit of a preferable temperature is 300° C., more preferably 200° C. If the reaction temperature is low then the reaction time for sufficient reaction becomes long, and if the reaction temperature is high then it becomes difficult to carry out formation processing.

Curing may be carried out at a fixed temperature, however the temperature may be changed in multiple stages or in a successive manner, if necessary. It is preferable that reaction is caused by raising the temperature in a multiple stage or in a consecutive manner rather than carrying out the reaction at a fixed temperature, since a cured product with fewer warps is more attainable.

Additives

Curing Retarder

A curing retarder may be used to improve storage stability or to adjust reactivity in the hydrosilylation reaction of the curable composition of the present invention. Examples of the curing retarder encompass compounds including an aliphatic unsaturated bond, organic phosphorous compounds, organic sulfuric compounds, nitrogen-contained compounds, tin-based compounds, organic peroxides and the like; these also may be used in combination.

Examples of a compound including an aliphatic unsaturated bond encompass: propargylalcohols such as 3-hydroxy-3-methyl-1-butyne, 3-hydroxy-3-phenyl-1-butyne, and 1-ethynyl-1-cyclohexanol; enyne compounds; and maleates such as dimethyl maleate. Examples of an organic phosphorous compound encompass: triorganophosphines, diorganophosphines, organophosphones, and triorganophosphites. Examples of an organic sulfuric compound encompass: organomercaptanes, diorganosuifides, hydrogen sulfide, benzothiazole, thiazole, and benzothiazole disulfide. Examples of the tin-based compound encompass: halogen tin (II) dihydrate, and tin (II) carboxylate. Examples of the organic peroxides encompass: di-t-butyl peroxide, dicumyl peroxide, benzoyl peroxide, and perbenzoic acid t-butyl.

Among these curing retarders, it is preferable to use benzothiazole, thiazole, dimethyl maleate, 3-hydroxy-3-methyl-1-butyne, or 1-ethynyl-1-cyclohexanol, in view of good retarding activity and availability of raw material.

The added amount of the curing retarders may be variously set, however a preferable lower limit of an added amount is $10^{-1}$ mol, more preferably 1 mol, and a preferable upper limit of the added amount is $10^3$ mol, more preferably 50 mol, each with respect to 1 mol of the used hydrosilylation catalyst.

Moreover, these curing retarders may be used solely, or two or more types thereof may be used in combination.

Adhesion Promoter

An adhesion promoter may be added to the curable composition of the present invention. Examples of the adhesion promoter that may be used include generally used adhesion promoters, various coupling agents, epoxy compounds, phenol resin, coumarone-indene resin, rosin ester resin, terpene phenol resin, α-methyl styrene-vinyltoluene copolymer, polyethyl methyl styrene, and aromatic polyisocyanate.

An included amount of the adhesion promoter is preferably in a range of 0.01 parts to 10 parts by weight, more preferably in a range of 0.05 parts to 5 parts by weight, and further preferably 0.1 parts to 2.5 parts by weight, each with respect to a total amount of components (A) and (B) as 100 parts by weight.

A coupling agent usable for the curable composition of the present invention is for example a silane coupling agent. The silane coupling agent is not particularly limited as long as it is a compound that has, per molecule, each of (i) at least one functional group that is reactive with an organic group and (ii) at least one hydrolysable silicon group. The group that is reactive with an organic group is at least one functional group preferably selected from the group consisting of: an epoxy group, a methacrylic group, an acrylic group, an isocyanate group, an isocyanurate group, a vinyl group, and a carbamate group in view of handling ability, and is particularly preferably an epoxy group, a methacrylic group, or an acrylic group, in view of curability and adhesivity. The hydrolysable silicon group is preferably an alkoxysilyl group in view of handling ability, and is particularly preferably a methoxysilyl group or an ethoxysilyl group in view of reactivity.

Examples of preferable silane coupling agents encompass: alkoxysilanes having an epoxy functional group, such as 3-glycidoxypropyl trimethoxysilane, 3-glycidoxypropyl triethoxysilane, 2-(3,4-epoxycyclohexyl) ethyltrimethoxysilane, and 2-(3,4-epoxycyclohexyl) ethyltriethoxysilane; and alkoxysilanes having a methacrylic group or an acrylic group, such as 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane, and acryloxymethyltriethoxysilane.

In a case where a silane coupling agent is used in the curable composition of the present invention, its added amount is sufficient as long as it is within the range of the included amount of the preferable adhesion promoter. More specifically, a lower limit of a preferable added amount is 0.1 parts by weight, more preferably 0.5 parts by weight, and an upper amount of the preferable added amount is 10 parts by weight, more preferably 5 parts by weight, each with respect to a total amount of the components (A) and (B) as 100 parts by weight. If the added amount is smaller, then no adhesivity improvement effect is apparent, and if the added amount is greater, an adverse effect may be given to the curing properties of the curable composition.

Examples of the epoxy compound encompass: novolac phenol-type epoxy resin, biphenyl-type epoxy resin, dicyclopentadiene-type epoxy resin, bisphenol-F diglycidyl ether, bisphenol-A diglycidyl ether, 2,2'-bis(4-glycidyloxy cyclohexyl) propane, 3,4-epoxycyclohexylmethyl-3,4-epoxycyclohexanecarboxylate, vinyl cyclohexene dioxide, 2-(3,4-epoxycyclohexyl)-5,5-spiro-(3,4-epoxycyclohexane)-1,3-dioxane, bis(3,4-epoxycyclohexyl)adipate, 1,2-cyclopropanedicarboxylic acid bisglycidyl ester, triglycidyl isocyanurate, monoallyl diglycidyl isocyanurate, and diallyl monoglycidyl isocyanurate.

In a case where the epoxy compound is used in the curable composition of the present invention, its added amount is sufficient as long as its included amount is within the preferable range of the added amount of the adhesion promoter. More specifically, a lower limit of the preferable added amount is 1 part by weight, more preferably 2 parts by weight, and an upper limit of the preferable added amount is 10 parts by weight, more preferably 5 parts by weight, each with respect to a total amount of the components (A) and (B) as 100 parts by weight. If the added amount is smaller then no adhesivity improvement effect is apparent, and if the added amount is greater then adverse effects may occur to the curing properties of the curable composition.

Moreover, these coupling agents, silane coupling agents, epoxy compounds and the like may be used solely, or two or more types thereof may be used in combination.

Moreover, with the present invention, in order to enhance the effect of the coupling agent and the epoxy compound, a silanol condensation catalyst may be further used, to improve and/or stabilize adhesivity.

Such a silanol condensation catalyst is not particularly limited, however it is preferable to use a boron-based compound or/and aluminum-based compound and/or titanium-based compound.

Examples of the boron-based compound used in the present invention encompass borates such as: tri-2-ethyl hexyl borate, n-trioctadecyl borate, tri-n-octyl borate, triphenyl borate, trimethylene borate, tris(trimethylsilyl)borate, tri-n-butyl borate, tri-sec-butyl borate, tri-tert-butyl borate, triisopropyl borate, tri-n-propyl borate, triallyl borate, triethyl borate, trimethyl borate, and methoxyethoxide borate.

Just one type of these borates may be used, or two or more types thereof may be used in combination. The borates may be mixed beforehand, or may be mixed when preparing the cured product.

Among the borates, it is preferable to use trimethyl borate, triethyl borate, or tri-n-butyl borate in view of availability and industrial practical use; the trimethyl borate is more preferable of these three borates.

In view of holding back volatilization upon curing, it is preferable to use n-trioctadecyl borate, tri-n-octyl borate, triphenyl borate, trimethylene borate, tris(trimethylsilyl)borate, tri-n-butyl borate, tri-sec-butyl borate, tri-tert-butyl borate, triisopropyl borate, tri-n-propyl borate, triallyl borate, or methoxyethoxide borate; among these, n-octadecyl borate, tri-tert-butyl borate, triphenyl borate, or tri-n-butyl borate is more preferably used.

In view of holding back volatilization and attaining good workability, it is preferable to use tri-n-butyl borate, triisopropyl borate, or tri-n-propyl borate; tri-n-butyl borate is more preferably used.

In view of less coloring under high temperature, it is preferable to use trimethyl borate or triethyl borate; trimethyl borate is more preferably used.

Examples of the aluminum-based compounds encompass: aluminum alkoxides such as aluminum triisopropoxide, sec-butoxy aluminum diisopropoxide, and aluminum tri-sec-butoxide; and aluminum chelates such as ethylacetoacetate aluminum diisopropoxide, aluminum tris(ethylacetoacetate), aluminum chelate M (manufactured by Kawaken Fine Chemicals Co., Ltd.: alkyl acetoacetate aluminum diisopropoxide), aluminum tris(acetylacetonate), and aluminum monoacetylacetonate bis(ethylacetoacetate). In view of handling ability, it is more preferable to use the aluminum chelates.

Examples of the titanium-based compounds encompass: tetraalkoxy titaniums such as tetraisopropoxy titanium and tetrabutoxy titanium; titanium chelates such as titanium tetraacetylacetonate; and general titanate coupling agents including residue such as oxyacetate and ethylene glycol.

In a case where the silanol condensation catalyst is used, its used amount may be set variously, however a lower limit of a preferable added amount is 0.1 parts by weight, more preferably 1 part by weight, and an upper limit of a preferable added amount is 50 parts by weight, more preferably 30 parts by weight, each with respect to 100 parts by weight of the coupling agent and/or epoxy compound. If the added amount is smaller then no adhesivity improvement effect is apparent, and if the added amount is greater then adverse effects may occur to the curing property of the curable composition.

Moreover, the silanol condensation catalysts may be used solely, or two or more types thereof may be used in combination.

In order to further enhance the adhesivity improvement effect, it is possible to further use a silanol source compound, for improving and/or stabilizing adhesivity. Examples of such a silanol source encompass: silanol compounds such as triphenyl silanol and diphenyldihydroxysilane; and alkoxysilanes such as diphenyl dimethoxysilane, tetramethoxysilane, and methyltrimethoxysilane.

In a case where the silanol source compound is used, its used amount may be set variously, however, a lower limit of a preferable added amount is 0.1 parts by weight, more preferably 1 part by weight, and an upper limit of the preferable added amount is 50 parts by weight, more preferably 30 parts by weight, each with respect to 100 parts by weight of the coupling agent and/or epoxy compound. If the added amount is smaller, no adhesivity improvement effect is apparent, and if the added amount is greater, adverse effects may occur to the curing property.

These silanol source compounds may be used solely, or two or more types thereof may be used in combination.

In order to enhance the effect of the coupling agent and epoxy compound, carboxylic acids and/or acid anhydrides may be used to improve and/or stabilize adhesivity. These carboxylic acids and acid anhydrides are not particularly limited, and examples encompass:

Chem. 47

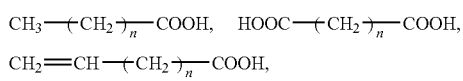

where n is a number of 0 to 30,

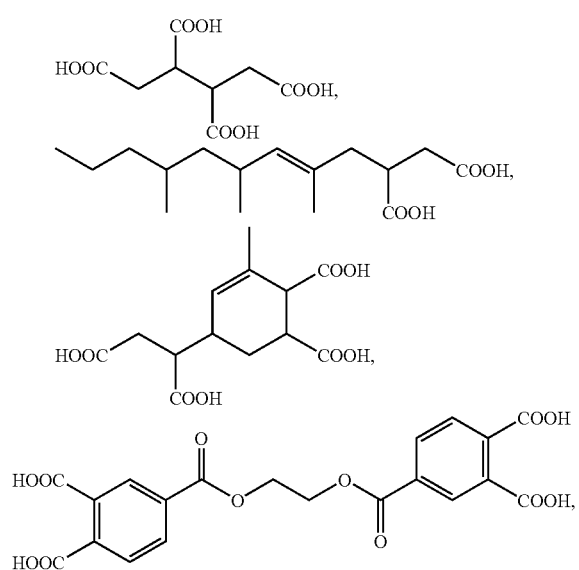

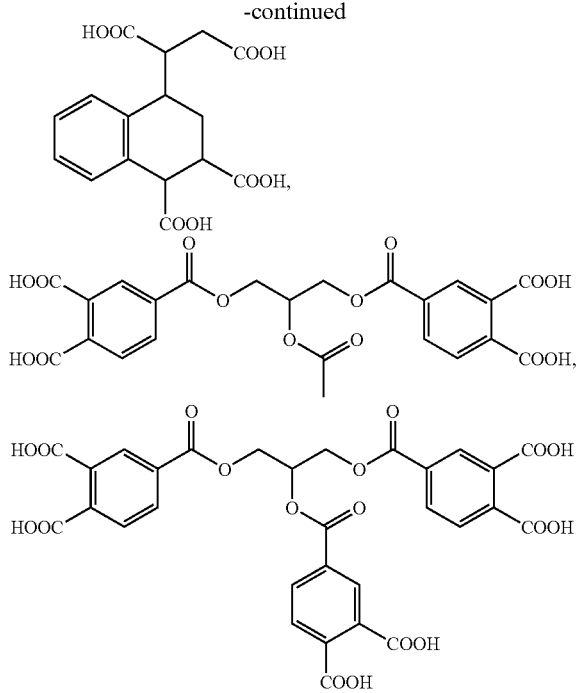

2-ethylhexanoic acid, cyclohexanecarboxylic acid, cyclohexanedicarboxylic acid, methylcyclohexanedicarboxylic acid, tetrahydrophthalic acid, methyltetrahydrophthalic acid, methyl hymic acid, norbornene dicarboxylic acid, hydrogenated methyl nadic acid, maleic acid, acetylenedicarboxylic acid, lactic acid, malic acid, citric acid, tartaric acid, benzoic acid, hydroxybenzoic acid, cinnamic acid, phthalic acid, trimellitic acid, pyromellitic acid, naphthalenecarboxylic acid, naphthalenedicarboxylic acid, and their independent or complex acid anhydrides.

Among these carboxylic acids and/or acid anhydrides, it is preferable to use ones which include a carbon-carbon double bond that is reactive with an SiH group, in view of attaining hydrosilylation reactivity, which carboxylic acids and/or acid anhydrides have a small possibility of leaking from an obtained cured product and causing less loss of physical property of the obtained cured product. Examples of preferable carboxylic acids and/or acid anhydrides encompass:

Chem. 48

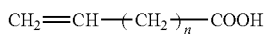

where n is a number of 0 to 30,
tetrahydrophthalic acid, methyltetrahydrophthalic acid, and their independent or complex acid anhydrides.

In a case where the carboxylic acids and/or acid anhydrides are used, its used amount may be set variously, however, a lower limit of a preferable added amount is 0.1 parts by weight, more preferably 1 part by weight, and an upper limit of the preferable added amount is 50 parts by weight, more preferably 10 parts by weight, each with respect to 100 parts by weight of the coupling agent and/or epoxy compound. If the added amount is smaller then no improvement effect of adhesivity becomes apparent, and if the added amount is greater then adverse effects may occur to the curing properties.

These carboxylic acids and/or acid anhydrides may be used solely or two or more types thereof may be used in combination.

Thermosetting Resin

To modify properties of the curable composition of the present invention, various thermosetting resins may be added. Examples of the thermosetting resin include, however is not limited to: epoxy resin, cyanate ester resin, phenolic resin, polyimide resin, urethane resin, and bismaleimide resin. Among these resins, the epoxy resin is preferable, in view of excellent practical properties such as adhesivity.

Examples of the epoxy resin encompass: epoxy resins such as novolac phenol-type epoxy resin, biphenyl-type epoxy resin, dicyclopentadiene-type epoxy resin, bisphenol-F diglycidyl ether, hydrogenated bisphenol-F diglycidyl ether, bisphenol-A diglycidyl ether, hydrogenated bisphenol-A diglycidyl ether, 2,2'-bis(4-glycidyloxy cyclohexyl)propane, 3,4-epoxycyclohexylmethyl-3,4-epoxycyclohexanecarboxylate, vinyl cyclohexene dioxide, 2-(3,4-epoxycyclohexyl)-5,5-spiro-(3,4-epoxycylcohexane)-1,3-dioxane, bis(3,4-epoxycyclohexyl)adipate, 1,2-cyclopropanedicarboxylic acid bisglycidyl ester, triglycidyl isocyanurate, monoallyl diglycidyl isocyanurate, or diallyl monoglycidyl isocyanurate, cured with an aliphatic acid anhydride such as hexahydrophthalic anhydride, methylhexahydrophthalic anhydride, trialkyltetrahydrophthalic anhydride, or hydrogenated methyl nadir anhydride. These epoxy resins or curing agents may be used solely, or a plurality thereof may be used in combination.

The thermosetting resin is not particularly limited in its added amount, however a lower limit of a preferable used amount is 5% by weight, more preferably 10% by weight of an entire curable composition, and an upper limit of a preferable used amount is 50% by weight, more preferably 30% by weight of the curable composition. If the added amount is smaller, it is difficult to attain the effect for adhesivity and the like, and if the added amount is greater, the curable composition becomes weaker.

These thermosetting resins may be used solely, or a plurality thereof may be used in combination.

The thermosetting resin may be mixed in the component (A) and/or component (B) by (i) dissolving raw resin material of the thermosetting resin and/or cured thermosetting resin into the component (A) and/or (B) to attain a mixture in an even state, (ii) crushing the thermosetting resin into particles and thereafter mixing with the component (A) and/or (B), or (iii) having the thermosetting resin being in a dispersed state by dissolving the thermosetting resin into a solvent and mixing the solvent with the component (A) and/or (B). In view of obtaining a more transparent cured product, it is preferable to mix by dissolving the raw material and/or cured thermosetting resin into the component (A) and/or (B). In this case also, the thermosetting resin may be directly dissolved into the component (A) and/or (B), be evenly mixed by using a solvent or the like, and thereafter be made into a dispersion state and/or a mixed state by removing the solvent thereafter.

In a case where the thermosetting resin is used by dispersing the thermosetting resin, an average particle diameter of the thermosetting resin may be set variously. However, a lower limit of a preferable average particle diameter is 10 nm, and an upper limit of the preferable average particle diameter is 10 μm. Distribution of particles can exist, and may be monodispersed or may have a plurality of peak particle diameters. However, in view that the curable composition attains low viscosity and good formation properties, it is preferable that a coefficient of variation is not more than 10%.

Thermoplastic Resin

It is possible to add various thermoplastic resins to the curable composition of the present invention for modifying properties of the curable composition and like purposes. Various thermoplastic resins may be used, and examples thereof include, however are not to: polymethylmethacrylate-based resin such as a methylmethacrylate homopolymer or a random, block or graft polymer of methylmethacrylate and another monomer (e.g., OPTOREZ manufactured by Hitachi Chemicals Co., Ltd.); acrylic resin whose typical example is a polybutyl acrylate resin of a butyl acrylate homopolymer or a random, block, or graft polymer of butyl acrylate and another monomer; a polycarbonate-based resin such as a polycarbonate resin including bisphenol-A, 3,3,5-trimethyl-cyclohexylidene bisphenol or the like as a monomer structure (e.g., APEC manufactured by TEIJIN Limited); a cycloorefin-based resin such as a resin in which a norbornene derivative, vinyl monomer, etc. is homopolymerized or copolymerized, a resin in which ring-opening methathesis polymerization is carried out to a norbornene derivative, or their hydrogenated object (e.g., APEL manufactured by Mitsui Chemicals, Inc.; ZEONOR and ZEONEX each manufactured by ZEON Corporation, ARTON manufactured by JSR Corporation); an orefin-maleimide-based resin such as a copolymer of ethylene and maleimide (e.g., TI-PAS manufactured by Tosoh Corporation); a polyester-based resin such as polyester in which bisphenols such as bisphenol-A and bis(4-(2-hydroxyethoxy)phenyl)fluorene or diols such as diethylene glycol is polycondensed with (i) phthalic acids such as terephthalic acid and isophthalic acid or (ii) aliphatic dicarboxylic acids (e.g., O-PET manufactured by Kanebo Ltd.); a polyether sulfone-based resin, polyalylate resin, polyvinyl acetal resin, polyethylene resin, polypropylene resin, polystyrene resin, polyamide resin, silicone resin, and fluororesin, and also rubber-form resin such as natural rubber and EPDM.

The thermoplastic resin may have, in its molecule, (i) a carbon-carbon double bond that is reactive with a SiH group and/or (ii) a SiH group. In view of attaining a stronger cured product, it is preferable to have per molecule an average of (i) at least one carbon-carbon double bond that is reactive with a SiH group, and/or (ii) the SiH group.

The thermoplastic resin may include other crosslinking groups. The crosslinking groups in this case include: an epoxy group, amino group, radically polymerized unsaturated group, carboxylic group, isocyanate group, hydroxyl group, and an alkoxysilyl group. In view of obtaining a cured product having a higher heat resistance, it is preferable that the thermoplastic resin includes, per molecule, an average of at least one crosslinking group.

A molecular weight of the thermoplastic resin is not particularly limited, however in view that the components (A) and (B) attain good compatibility, it is preferable that a number-average molecular weight is not more than 10000, more preferably not more than 5000. On the opposite, in view of obtaining a firm cured product, the number-average molecular weight is at least 10000, more preferably at least 100000. A molecular weight distribution is also not particularly limited, however in view of attaining a mixture having a low viscosity and good formability, the molecular weight distribution is preferably not more than 3, is more preferably not more than 2, and is further preferably not more than 1.5.

A load of the thermoplastic resin is not particularly limited, however a lower limit of a preferably used amount is 5% by weight of an entire curable composition load, more preferably 10% by weight thereof, and an upper limit of the preferably used amount is 50% by weight of the entire curable composition load, more preferably 30% by weight thereof. If the added amount is smaller then the cured product obtained becomes brittle, and if the amount is greater the heat resistance (elasticity at a high temperature) easily decreases.

A sole thermoplastic resin may be used, or a plurality of thermoplastic resins may be used in combination.

The thermoplastic resin may be mixed in the component (A) and/or component (B) by (i) dissolving raw resin material of the thermoplastic resin and/or cured thermoplastic resin into the component (A) and/or (B) to attain a mixture in an even state, (ii) crushing the thermoplastic resin into particles and thereafter mixing with the component (A) and/or (B), or (iii) having the thermosetting resin being in a dispersed state by dissolving the thermoplastic resin into a solvent and mixing the solvent with the component (A) and/or (B). In view of obtaining a more transparent cured product, it is preferable to mix the raw material and/or cured thermoplastic resin by dissolving the raw material and/or cured thermoplastic resin into the component (A) and/or (B). In this case also, the thermoplastic resin may be directly dissolved into the component (A) and/or (B), be evenly mixed by using a solvent or the like, and be made into a dispersion state and/or a mixed state by removing the solvent thereafter.

In a case where the thermoplastic resin is used by dispersing the thermoplastic resin, an average particle diameter of the thermoplastic resin may be set variously. However, a lower limit of a preferable average particle diameter is 10 nm, and an upper limit of the preferable average particle diameter is 10 μm. Distribution of particles can exist, and may be monodispersed or may have a plurality of peak particle diameters. However, in view that the curable composition attains low viscosity and good formation properties, it is preferable that a coefficient of variation is not more than 10%.

Filler

A filler may be added to the curable composition of the present invention if necessary.

Various fillers may be used as the filler, for example: silica-based fillers such as quartz, fume silica, precipitated silica, silica anhydride, molten silica, crystalline silica, and ultrafine amorphous silica; inorganic fillers such as silicon nitride, silver powder, alumina, ammonium hydroxide, titanium oxide, glass fiber, carbon fiber, mica, carbon black, graphite, diatom earth, white earth, clay, talc, calcium carbonate, magnesium carbonate, barium sulfate, and inorganic balloon and fillers that are generally used and/or proposed as fillers of conventional sealing material such as epoxy.

Color Protecting Agent

A color protecting agent may be added to the curable composition of the present invention. Other than a generally used color protecting agent such as a hindered phenol-based color protecting agent or the like, citric acid, phosphorous acid, and sulfur-based color protecting agent may be used as the color protection agent.

As the hindered phenol based color protection agent, various agents may be used such as IRGANOX 1010, IRGANOX 1076, IRGANOX 330 available from Ciba Specialty Chemicals Inc., 2,6-di-t-butyl-4-methylphenol, and tris(3,5-di-butyl-4-hydroxybenzyl)isocyanurate.

As a sulfur-based color protecting agent, various agents may be used such as dilauryl-3,3'-thiodipropionate, dimyristyl-3,3'-thiodipropionate, distearyl-3,3'-thiodipropionate, and pentaerythritol tetrakis(3-laurylthiopropionate). Examples of the sulfur-based color protecting agent encompass: mercaptans, mercaptan salts, sulfide carboxylates, sulfides including hindered phenol sulfides, polysulfides, dithiocarboxylates, thioureas, thiophosphates, sulfonium compounds, thioaldehydes, thioketones, mercaptals, mercaptols, monothio acids, polythio acids, thioamides, and sulfoxides.

Various phosphorous color protecting agents are usable as the phosphorous color protecting agents, such as tris-nonylphenyl phosphite, distearyl pentaerythritol diphosphite, and tris(2,4-di-t-butylphenyl) phosphite.

Moreover, these color protecting agents may be used solely, or two or more types thereof may be used in combination.

An added amount of the color protecting agent may be set variously, however, a lower limit of a preferable added amount is 0.01 parts by weight, more preferably 0.1 parts by weight, and an upper limit of a preferable added amount is 10 parts by weight, more preferably 5 parts by weight, each with respect to a total amount of the components (A) and (B) as 100 parts by weight. If an added amount is smaller then no color protecting effect becomes apparent, and if the added amount is greater then an adverse effect may occur to the curing properties of the curable composition.

Radical Inhibiting Agent

A radical inhibiting agent may be added to the curable composition. Examples of the radical inhibiting agent encompass: phenolic radical inhibiting agents such as 2,6-di-t-butyl-3-methylphenol (BHT), 2,2'-methylene-bis(4-methyl-6-t-butylphenol), and tetrakis(methylene-3 (3,5-di-t-butyl-4-hydroxyphenyl)propionate)methane; and amine-based radical inhibiting agents such as phenyl-β-naphthylamine, α-naphthylamine, N,N'-sec-butyl-p-phenylenediamine, phenothiazine, and N,N'-diphenyl-p-phenylenediamine.

These radical inhibiting agents may be used solely, or two or more types thereof may be used in combination.

Ultraviolet Ray Absorbing Agent

An ultraviolet ray absorbing agent may be added to the curable composition. Examples of the ultraviolet ray absorbing agent encompass: 2(2'-hydroxy-3',5'-di-t-butylphenyl) benzotriazole, and bis(2,2,6,6-tetramethyl-4-piperidine) sebacate. These ultraviolet ray absorbing agents may be used solely, or two or more types thereof may be used in combination.

Other Additives

To the curable composition of the present invention, other additives such as a coloring agent, mold lubricant, flame retarder, flame retardant assistant, surfactant, antifoaming agent, emulsifying agent, leveling agent, anti-cissing agent, ion trapping agents such as antimony-bismuth, thixotropy promoter, adhesion promoter, storage stability improving agent, antiozonant, light stabilizing agent, thickening agent, plasticizing agent, reactive diluent, anti-oxidizing agent, heat stabilizing agent, electrical conductivity promoter, antistatic agent, radiation blocking agent, nucleating agent, phosphorous peroxide decomposing agent, lubricant, pigment, metal deactivator, thermal conductivity promoter, and physical property adjusting agent may be added, within a range in which the object and effect of the present invention is not lost.

Solvent

The curable composition obtained by the present invention may be used by dissolving the curable composition in a solvent. A usable solvent is not particularly limited, and suitably used examples thereof encompass: hydrocarbon-based solvents such as benzene, toluene, hexane, and heptane; ether-based solvents such as tetrahydrofuran, 1,4-dioxane, 1,3-dioxolane, and diethyl ether; ketone-based solvents such as acetone, methyl ethyl ketone, and methyl isobutyl ketone; and halogen-based solvents such as chloroform, methylene chloride, and 1,2-dichloroethane.

The toluene, tetrahydrofuran, 1,3-dioxolane, and chloroform are preferably used as the solvent.

An amount of solvent used may be set as appropriate, however a lower limit of a preferably used amount is 0.1 mL, and an upper limit of a preferably used amount is 10 mL, each with respect to 1 g of the curable composition. If the used amount is smaller, effect of using a solvent such as attainment of low viscosity becomes difficult to attain, and use of a great amount of solvent causes the solvent to remain in the material, thereby causing problems such as thermal cracking, and also is disadvantageous in terms of costs, thereby decreasing the value in industrial use.

These solvents may be used solely, or two or more solvents may be used as a mixed solvent.

The curable composition or cured product of the present invention may be used for various purposes.

Optical material as denoted in the present invention indicates material at large that is used for purposes to transmit light therethrough. Examples of the light to be transmitted therethrough are visible light, infrared ray, ultraviolet ray, X-ray, and laser.

Examples of such an optical material encompass: material used for liquid crystal display devices such as a color filter protective film, TFT flattening film, and substrate material; and material used for a light emitting diode (LED) such as a sealing agent and dye bond.

In the liquid crystal display field, examples of the optical material encompass: substrate material, light guide plate, prism sheet, deflection plate, phase plate, viewing angle compensation film, polarizer protective film, and color filter, and also various coating agents, protective films, sealing agents, adhesives and the like that are used with the material.

Moreover, other examples include material used in an LED display device such as a molding agent of an LED element, LED sealing agent, front glass protective film, and front glass substitute material, and also various coating agents, protective films, sealing agents, adhesives and the like used with the material.

Moreover, examples used in a color PDP (plasma display) include an antireflection film, optical compensation film, housing material, front glass protective film, and front glass substitute material, and also various coating agents, protective films, sealing agents, adhesives and the like used with the optical material. Further, examples used in a plasma address liquid crystal (PALC) display include a substrate material, light guide plate, prism sheet, deflection plate, phase plate, viewing angle compensation film, and polarizer protective film, and also various coating agents, protective films, sealing agents, adhesives and the like used with the optical material. Moreover, examples used in an organic EL (electroluminescence) display include a front glass protective film, and front glass substitute material, and also various coating agents, protective films, sealing agents, adhesives and the like used with these optical materials. Moreover, in a field emission display (FED), examples used include various film substrates, front glass protective film, and front glass substitute material, and also various coating agents, protective films, sealing agents, adhesives and the like used with such a material. Moreover, material used in an electronic paper such as a transparent film, various coating agents, protective films, sealing agents, adhesives and the like are also examples of the optical material.

Furthermore, in the optical recording field, other examples encompass: disk substrate material for VD (video disk), CD/CD-ROM, CD-R/RW, DVD-R/DVD-RAM, MO/MD, PD (phase change disk), BD (Blue-ray Disk), hologram optical cards, pick-up lens, protective films, and various coating agents, protective films, sealing agents, adhesives and the like used with the foregoing optical material.

In the optical device field, examples encompass: lens material, finder prism, target prism, finder cover, and light-receiving sensor of a steel camera, and various coating agents, protective films, sealing agents, adhesives and the like used with the optical material. Moreover, examples also include photographing lens and finder of a video camera, and various coating agents, protective films, sealing agents, adhesives and the like used therewith. Further, examples also include projector lens and protective films of a projection television and various coating agents, protective films, sealing agents, adhesives and the like used therewith. Lens material and various films of an optical sensing device, and various coating agents, protective films, sealing agents, adhesives and the like used therewith are also further examples of the optical material.

In the optical component field, examples encompass: fiber material, lens, waveguide, and elements, each provided around an optical switch in an optical communication system, and various coating agents, protective films, sealing agents, adhesives and the like used with the optical material. Examples further encompass optical fiber material and ferrule around an optical connector and various coating agents, protective films, sealing agents, adhesives and the like used with the optical material. With optical passive components and optical circuit components, examples encompass a lens and a waveguide, and various coating agents, protective films, sealing agents, adhesives and the like used with the optical material. Examples also include substrate material and fiber material around an optoelectronic integrated circuit (OEIC), and various coating agents, protective films, sealing agents, adhesives and the like used with the optical material.

In the optical fiber field, examples encompass: optical fibers used for (i) industrial sensors such as ornamental display lighting/light guide, (ii) display/signs, and (iii) communication infrastructure and domestic digital device connection, and also various coating agents, protective films, sealing agents, adhesives and the like used with the optical material.

In the coating field, material for paint, UV powder paint, ink, coloring ink, and UV inkjet ink are also examples of the optical material.

Examples of photoresist material include: resist material, liquid resist material, coloring resist, dry film resist material, solder resist material, and laser beam lithography material.

Resist material for microlithography of LSI and VLSI material as peripheral material for semiconductor integrated circuits are also another example of the optical material.

In the automobile/transport field, lamp material such as head, tail and interior lamps of an automobile, various interior and exterior ornaments such as a lamp reflector, lamp lens, outer casing/interior panels, glass substitutes and various coating agents, protective films, sealing agents, adhesives and the like used as the glass substitutes are examples of the optical material. Moreover, outer casing components and glass substitutes of railway vehicles, and various coating agents, protective films, sealing agents, adhesives and the like used with the optical material are also examples of the optical material. Further, outer casing components and glass substitutes of airplanes, and various coating agents, protective films, sealing agents, adhesives and the like used with the material are also examples of the optical material.

In the architecture field, glass intermediate films, glass substitutes, solar cell peripheral material and various coating agents, protective films, sealing agents, adhesives and the like used with the material are further examples of the optical material.

House coating film is also an example in agricultural use.

Examples of next generation optic and electric functional organic material encompass: organic EL element peripheral material, organic photorefractive elements, light amplifying element which is a light-light transforming device, optical operation element, peripheral substrate material of organic solar cell, fiber material, sealing agent of elements and various coating agents, protective films, sealing agents, adhesives and the like used with the optical material.

Other uses except for using as a dicing tape, photoreceptor drum for a copying machine, contact lens and optical material, are for example: insulating material made of electronic material (including printed board, electric wire coating, etc.), high voltage insulating material, interlayer insulating film, insulation packing, insulating coating material, electric material sealing material, high heat resistant adhesive, high heat-releasing adhesive, adhesives for various substrates, adhesives for heat sinks, sealing material, potting material, fuel cell material, battery solid electrolyte, gas separation film, forming material (including sheet, film, FRP, etc.), vibration-proof material, water-proof material, damp-proof material, heat shrinkable rubber tube, O-ring, or additives for concrete protective agent, lining, soil injection agent, cool storage medium, sterilization processing device sealing material and other resins.

EXAMPLES

The following description explains Examples and Comparative Examples of the present invention. However, the present invention is not limited to these Examples.

The following description explains a Synthesis Example and Rectification Example of (β1) and (β2) which are cyclic polyorganosiloxanes of the present invention. Contents of components of the cyclic polyorganosiloxane were measured by gas chromatography in the following method.

Analysis Method

A cyclic polyorganosiloxane obtained by heating and distilling a chain polyorganosiloxane in the presence of a catalyst was analyzed by gas chromatography. The cyclic polyorganosiloxane was represented by the following general formula (XI):

Chem. 49

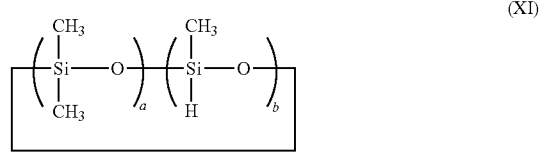

Each component was measured based on a detection sensitivity of 1,3,5,7-tetramethylcyclotetrasiloxane (a,b)=(0,4), 1,1,3,3,5,5,7,7-octamethylcyclotetrasiloxane (a,b)=(4,0), 1,1,3,3,5,5-hexamethylcyclotrisiloxane (a,b)=(3,0), and 1,3,5,7,9-pentamethylcyclopentasiloxane (a,b)=(0,5), each of which are available as authentic preparations; (a,b)=(1,3), (2,2), (3,1) were measured by proportionally distributing the detection sensitivity of (0,4) and (4,0). Moreover, since detection sensitivities of (a,b)=(0,4) and (a,b)=(0,5) were the same, (a,b)=(0,3) was also treated as having an identical detection sensitivity, and (a,b)=(2,1) was measured by similarly proportionally distributing the detection sensitivity of (a,b)=(0, 3).

A molar ratio of $(CH_3)_2SiO$ unit and $CH_3HSiO$ unit of the chain polyorganosiloxane which was the raw material was calculated by an NMR method, which molar ratio was calculated from peaks of the SiH group and SiCH$_3$ group.

Synthesis Example 1

A four-necked round bottom flask having a capacity of 500 mL provided with a thermometer, magnetic stirring bar, distillation tube having a rectifying tower (Vigreaux-type, 20 cm), and a distillate catch-and-storing device, was connected to a decompressed pump via a trap. Into the flask, (i) 290 g of (CH$_3$)$_3$SiO—((CH$_3$)$_2$SiO)$_m$—((CH$_3$)HSiO)$_n$—Si(CH$_3$)$_3$ (((n/(m+n)) was 0.52) (HMS-501 manufactured by Gelest Inc.) having a molecular weight of 900 to 1200 and a CH$_3$HSiO unit of 52 mol % and (ii) 1.45 g of aluminum triisopropoxide were added, and this mixture was heated for 30 minutes in an oil bath of 190 torr at 200° C. Thereafter, a distillate was collected which was distilled at 100° C. to 80° C. under a decompression degree of 160 to 50 torr. After confirming that an overhead temperature has decreased due to the decrease in amount of the distillate, the reaction was terminated. The total amount of the collected distillate was 200 g (69% yield), and 154 g (53% yield) was obtained as a main distillate.

Synthesis Comparative Example 1

A four-necked round bottom flask having a capacity of 500 mL provided with a thermometer, magnetic stirring bar, distillation tube having a rectifying tower (Vigreaux-type, 20 cm), and a distillate catch-and-storing device, was connected to a decompressed pump via a trap. Into the flask, (i) 350 g of (CH$_3$)$_3$SiO—((CH$_3$)$_2$SiO)$_m$—(CH$_3$)HSiO)$_n$—Si(CH$_3$)$_3$ (((n/(m+n)) was 0.27) (HMS-301 manufactured by Gelest Inc.) having a molecular weight of 1900 to 2000 and a CH$_3$HSiO unit of 27 mol % and (ii) 1.50 g of aluminum triisopropoxide were added, and this mixture was heated for 30 minutes in an oil bath of 190 torr and 200° C. Thereafter, a distillate was collected which was distilled at 100° C. to 80° C. under a decompression degree of 120 to 50 torr. After confirming that an overhead temperature has decreased due to the decrease in amount of distillate, the reaction was terminated. The total amount of the collected distillate was 133 g (38% yield), and 109 g (31% yield) was obtained as a main distillate. Table 1 shows a result of analyzing the actual distillates of Synthesis Example 1 and Synthesis Comparative Example 1 by gas chromatography.

TABLE 1

| Component | a + b<br>b | 3<br>1 | 3<br>0 | 4<br>4 | 4<br>3 | 4<br>2 | 4<br>1 | 5<br>0 | 5<br>5 | yield<br>(%) |
|---|---|---|---|---|---|---|---|---|---|---|
| S. Ex. 1 | wt % | 7 | 4 | 8 | 29 | 30 | 13 | 0.6 | 0.2 | 52.6 |
| S. C. Ex. 1 | wt % | 5 | 1 | 6 | 16 | 33 | 31 | 1 | 1 | 31.4 |

(S. Ex.: Synthesis Example; S. C. Ex.: Synthesis Comparative Example)

As shown in Table 1, when the molar ratio (n/(m+n)) defined in the present invention falls below 0.3, i.e., when the CH$_3$HSiO unit in the chain polyorganosiloxane which is the raw material is small in amount, the number of cyclic polyorganosiloxane which has one SiH group per molecule tends to increase, while a total amount of distillate (yield) tends to decrease. The cyclic polyorganosiloxane that has one SiH group per molecule does not cross-link, and therefore is preferably small in number. Moreover, a low total amount of distillate (yield) causes a drop in productivity, and therefore is disadvantageous. On the other hand, if the molar ratio (n/(m+n)) defined in the present invention exceeds 0.9, the amount of cyclic polyorganosiloxane in which the SiH group is not reduced increases in number. This makes it impossible to attain the crack resistance which is an effect of the present invention. Therefore, it is clear with the method of the present invention that it is possible to selectively produce in high yield a cyclic polyorganosiloxane in which a desired SiH group is reduced.

A target cyclic polyorganosiloxane is concentrated by further rectifying a distillate that was obtained by heating and distilling a chain polyorganosiloxane in the presence of a catalyst.

Rectification

A four-necked round bottom flask having a capacity of 500 mL provided with a thermometer, magnetic stirring bar, distillation tube having a rectifying tower (Vigreaux-type, 20 cm), and a distillate catch-and-storing device, was connected to a decompressed pump via a trap. In the flask, (1) 180 g of distillate of Synthesis Example 1, and (ii) 100 g of distillate of Synthesis Comparative Example 1 were added, and this mixture was heated for 60 minutes in an oil bath at 190 torr and 100° C. Thereafter, foreshots that were distilled at a liquid temperature of 90° C. to 100° C., 120 to 100 torr, and overhead temperature of 70° C. to 80° C. were collected, then actual distillates distilled at a liquid temperature of 90° C. to 100° C., 100 to 90 torr, and overhead temperature of 80° C. to 90° C. were collected. The collected fore shot was 75 g (26.8% yield), the main distillate was 94 g (33.6% yield), and an amount remaining in the flask was 111 g (39.6% yield). Table 2 shows a result of analyzing the liquid inside the flask which has not been rectified and the obtained main distillation liquid, by gas chromatography.

TABLE 2

| Component | a + b<br>b | 3<br>1 | 3<br>0 | 4<br>4 | 4<br>3 | 4<br>2 | 4<br>1 | 4<br>0 | 5<br>5 |
|---|---|---|---|---|---|---|---|---|---|
| Liquid in Flask before rectification | wt % | 9.9 | 4.0 | 3.8 | 18.6 | 33.1 | 28.8 | 1.6 | 0.3 |
| Main Distillate liquid | wt % | 0.3 | 2.6 | 3.0 | 42.0 | 42.9 | 9.0 | 0.2 | 0.1 |

Table 2 shows that content of (β1) and (β2) in the cyclic polyorganosiloxane which has not been rectified is a total of 51.7 wt %, and that this concentration increases to 84.9 wt % by the rectification.

Synthesis examples of modified polyorganosiloxane compounds (B) are shown in Synthesis Example 2 and Synthesis Comparative Examples 2 and 3. The reaction tracking in the synthesis of the component (B), and viscosity and SiH group value of the component (B) were measured as follows.

NMR

A 300 MHz NMR device manufactured by Varian Technologies Japan Limited was used. Reaction tracking of the component (B) synthesis was obtained by (i) diluting a reaction liquid with heavy chloroform to around 1%, (ii) adding this diluted liquid into an NMR tube to measure a peak of a methylene group derived from a non-reacted allyl group and a peak of a methylene group derived from a reacted allyl group, and (iii) calculating the reaction tracking from the two peaks. Moreover, as a functional group value of the (B) component, a SiH group value (mmol/g) was calculated by dibromoethane conversion.

Viscosity

An E-type viscometer manufactured by Tokyo Keiki Inc. was used. Measurement was made at a measuring temperature of 23° C., and with use of an EHD-type 48φ cone.

Synthesis Example 2

To a four-necked round bottom flask having a capacity of 500 mL provided with a thermometer, magnetic stirring bar, reflux tower, and a dropping funnel, (i) 86.3 g of main distillation liquid obtained by rectification and (ii) 143.3 g of toluene were added, and this mixture was heated and stirred at a bath temperature of 105° C. under nitrogen air flow. Then, an evenly mixed liquid of (i) 23.0 g of triallyl isocyanurate, (ii) 23.0 g of toluene and (iii) 0.0182 g of xylene solution of platinum vinylsiloxane complex (including 3 wt % of platinum), was dropped into the flask for 80 minutes. After 1 hour had elapsed since termination of dropping, it was confirmed by NMR measurement that a reaction rate of the allyl group was not less than 95%. Accordingly, the reaction was terminated by cooling the mixture. Non-reacted cyclic polyorganosiloxane, low molecular weight chain polyorganosiloxane, and toluene were distilled under reduced pressure, to obtain 71 g of a colorless, transparent liquid.

The obtained product was NMR measured, whereby a result was obtained that a part of the SiH group of (β1) and/or (β2) which reacted with an allyl group of triallyl isocyanurate was a main component of the obtained product, and that the obtained product includes 4.0 mmol/g of SiH group. A viscosity of the obtained product was 120 Pa·s.

Chem. 50

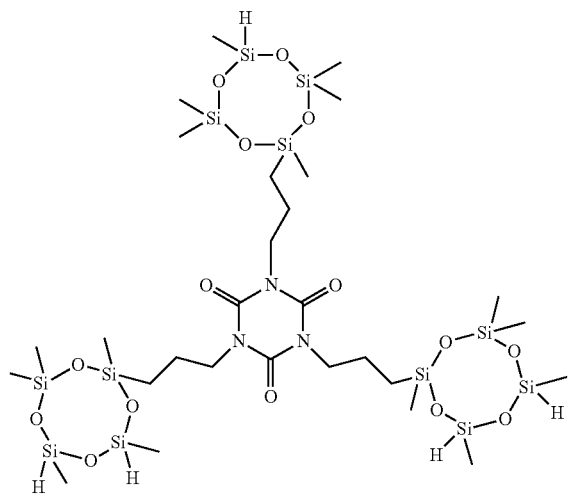

Synthesis Comparative Example 2

In an autoclave having a capacity of 2 L, (i) 602 g of toluene and (ii) 626 g of 1,3,5,7-tetramethylcyclotetrasiloxane were poured, and its gas phase section was substituted by nitrogen. Thereafter, this mixture was heated and stirred at a jacket temperature of 105° C. Then, a mixed liquid of (i) 90 g of triallyl isocyanurate, (ii) 90 g of toluene, and (iii) 0.057 g of xylene solution of platinum vinylsiloxane complex (including 3 wt % of platinum), was dropped into the autoclave for 40 minutes. After 4 hours elapsed since termination of dropping, it was confirmed by NMR measurement that a reaction rate of the allyl group was at least 95%. Then, the reaction was terminated by cooling the mixture. The non-reacted 1,3,5,7-tetramethylcyclotetrasiloxane and toluene were distilled under reduced pressure, to obtain a colorless, transparent liquid.

The obtained product was NMR measured, and obtained a result that a part of the SiH group in 1,3,5,7-tetramethylcyclotetrasiloxane were ones which reacted with the allyl group of triallyl isocyanurate, and that the obtained product included 8.6 mmol/g of SiH group. A viscosity of the obtained product was 2 Pa·s.

Chem. 51

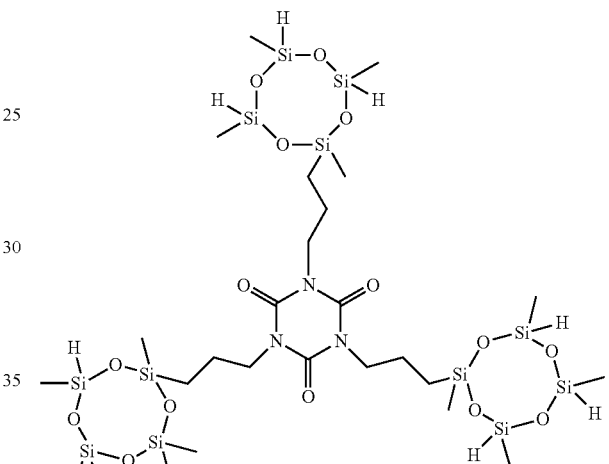

Synthesis Comparative Example 3

To a four-necked round bottom flask of a capacity of 1 L and having thermometer, magnetic stirring bar, reflux tower, and dropping funnel, (i) 150 g of a reactant obtained in Synthesis Comparative Example 2, and (ii) 450 g of toluene were poured, and this mixture was heated and stirred at a bath temperature of 105° C. under nitrogen air flow. To this mixture, an evenly mixed liquid of (i) 70.0 g of allyl glycidyl ether and (ii) 70.0 g of toluene was dropped for 40 minutes. After 1.5 hours since termination of dropping, it was confirmed by NMR measurement that a reaction rate of the allyl group was at least 95%. Then, the reaction was terminated by cooling the mixture. The toluene in the solvent was distilled under reduced pressure, to obtain 210 g of colorless, transparent liquid.

An obtained reactant was NMR measured, and obtained a result that a part of the SiH group of the reactant of Synthesis Comparative Example 2 was one which reacted with an allyl group in allyl glycidyl ether, and that the obtained reactant included 3.7 mmol/g of SiH group. A viscosity of the obtained reactant was 6 Pa·s.

Chem. 52

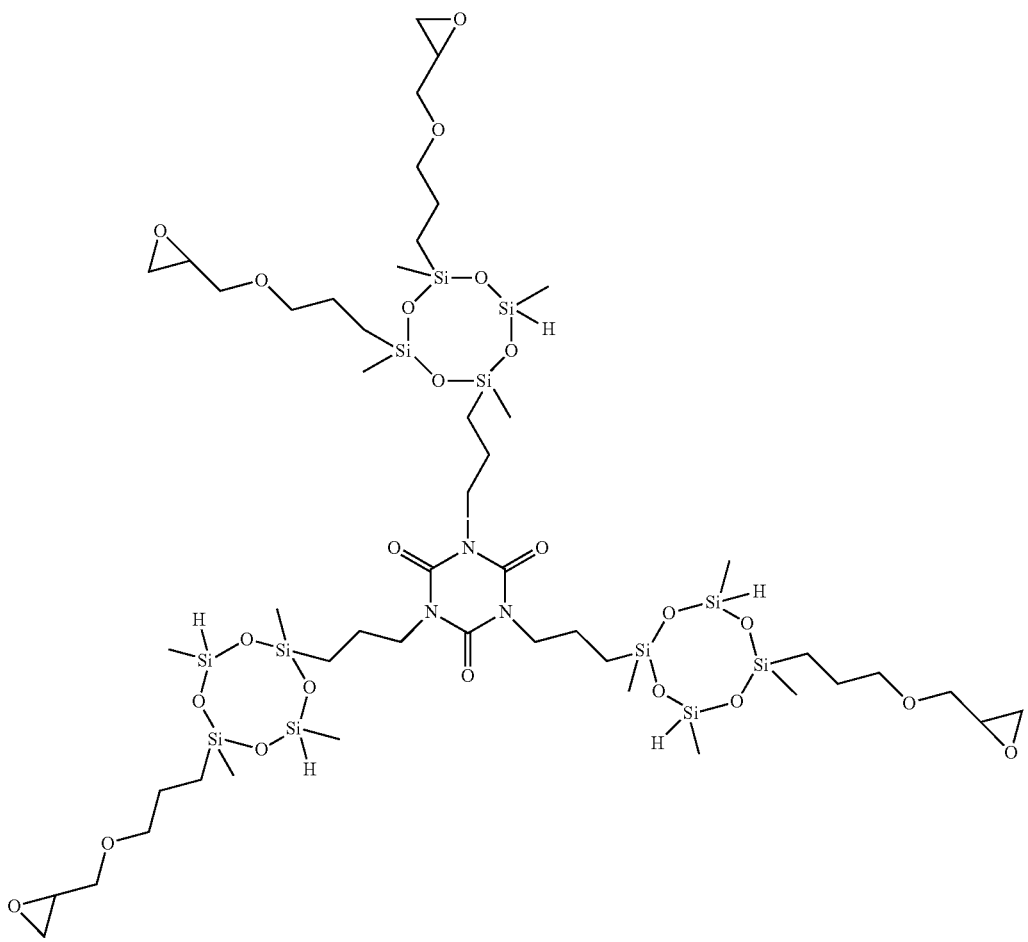

Gelling time of the curable composition prepared in Example 1 and Comparative Examples 1 and 2, and glass transition temperature, light transmittance, heat and light resistance test, and crack resistance test of the cured product were calculated or performed as follows:

Cured Product Appearance

A prepared sample strip having a thickness of 3 mm was placed on white paper, and was evaluated by visual inspection.

Gelling Time

On a hot plate set at 115±2° C., one drop (0.015±0.005 g) of the curable composition was dropped and was stirred at a fixed rate with a toothpick. How long the curable composition took to cure from when the curable composition was dropped on the hot plate was determined as the gelling time.

Glass Transition Temperature

A sample strip of a size 30 mm×5 mm×3 mm was cut out from the prepared cured product, and dynamic viscoelasticity was measured with DVA-200, manufactured by IT Keisoku Seigyo K.K., under the conditions of: tension mode; measurement frequency of 10 Hz; warp 0.1%; static/dynamic ratio: 1.5; and temperature increase rate of 5° C./min. A peak temperature of tan δ was determined as the glass transition temperature of the cured product.

Light Transmittance

A sample strip of a size 30 mm×10 mm×3 mm was cut out from the cured product, and was measured by using U-3300 manufactured by Hitachi Co., Ltd., under a condition of a scanning speed of 300 nm/min.

Heat and Light Resistance Test

A sample strip of a size 30 mm×10 mm×3 mm was cut out from a cured product, and light transmittance was measured by using Metaling weather meter M6T, manufactured by Suga Test Instruments Co., Ltd., having an inner temperature of 105° C., with an irradiance of 0.53 kW/m$^2$, after irradiating up to an accumulated irradiance of 50 MJ/m$^2$.

Crack Resistance Test

A sample strip of a size 30 mm×5 mm×3 mm was cut out from a cured product, and after immersing the sample in a solder bath at 280° C. for 10 seconds, then immediately immersing the sample into an ice water bath at not more than 5° C. for 10 seconds, presence of a crack in the cured product was observed.

Example 1 and Comparative Examples 1, 2

By using triallyl isocyanurate (TAIC) as the component (A), the reactant obtained in Synthesis Example 2 and Synthesis Comparative Examples 2 and 3 as the component (B), and xylene solution of platinum-divinyltetramethyldisiloxane complex (including 3 wt % of platinum) (PTVTS) as the component (C), a curable composition was prepared having a blend as shown in Table 3. How the components were blended were as follows: the component (A) and the component (C)

were mixed together and stirred to obtain an evenly mixed liquid, then to this mixed liquid, the component (B) and 1-ethynylcyclohexanol (1-ECH) were mixed together, then stirred and degassed, thereby obtaining a curable composition. This curable composition was poured into a cell that was prepared by providing two glass plates and inserting a silicon rubber sheet having a thickness of 3 mm as a spacer between the two glass plates. This curable composition poured into the cell was heated at 60° C. for 6 hours, 70° C. for 1 hour, 80° C. for 1 hour, 100° C. for 1 hour, 120° C. for 1 hour, 150° C. for 1 hour, and 180° C. for 30 minutes. This obtained a cured product.

An evaluation result of the obtained cured product is as shown in Table 3.

improved as compared to Comparative Example 1, the heat and light resistant transparency clearly decreased. It is considered that the cause for this decrease in heat and light resistant transparency is the increase in amount of organic components in the cured product. From the above results, it was suggested that a cured product synthesized by using a cyclic polyorganosiloxane reduced in SiH group as the modified polyorganosiloxane compound is effective for improving crack resistance and heat and light resistant transparency; and among these, use of the cyclic polyorganosiloxane that includes the components (β1) and (β2) attains a cured product having excellent crack resistance, while preventing loss of heat and light resistant transparency.

TABLE 3

|  |  | Ex. 1 | C. Ex. 1 | C. Ex. 2 |
|---|---|---|---|---|
| Content proportion (parts by weight) | TAIC | 24.2 | 40.2 | 22.6 |
|  | S. Ex. 2 | 75.8 |  |  |
|  | S. C. Ex. 2 |  | 59.8 |  |
|  | S. C. Ex. 3 |  |  | 77.4 |
|  | PTVTS | 0.10 | 0.20 | 0.20 |
|  | 1-ECH | 0.20 | 0.20 | 0.20 |
| Measurement/Evaluation Results | Appearance of curable composition | Colorless, transparent | Colorless, transparent | Colorless, transparent |
|  | Gelling time @115° C. (sec) | 16 | 24 | 19 |
|  | Glass transition temperature (° C.) | 145 | 147 | 102 |
|  | Light transparency before test (% T) |  |  |  |
|  | (400 nm) | 91 | 90 | 91 |
|  | (450 nm) | 93 | 92 | 92 |
|  | (470 nm) | 93 | 92 | 92 |
|  | Light transparency after heat and light resistance test (% T) |  |  |  |
|  | (400 nm) | 85 | 88 | 48 |
|  | (450 nm) | 89 | 91 | 61 |
|  | (470 nm) | 90 | 91 | 65 |
|  | Cooling impact test (between 280° C. and 5° C.) | ○ n = 3 No crack | X n = 3 All cracked | Δ n = 3 One crack |

(○ = good, X = poor, Δ = satisfactory)
(Ex.: Example; C. Ex.: Comparative Example; S. Ex.: Synthesis Example; S. C. Ex: Synthesis Comparative Example)

Table 3 shows that a cured product that uses a reactant of the cyclic polyorganosiloxane including the component (β1) and the component (β2) of Example 1 (Synthesis Example 2) retains a heat and light resistant transparency and has excellent crack resistance while hardly reducing the glass transition temperature, as compared to the cured product that uses the reactant of 1,3,5,7-tetramethylcyclotetrasiloxane of Comparative Example 1 (Synthesis Comparative Example 2). It is considered that if the 1,3,5,7-tetramethylcyclotetrasiloxane is used, the crosslinking density becomes too high, thereby attaining a low crack resistance. Accordingly, in order to decrease the crosslinking density, Comparative Example 2 prepared a cured product by using a reactant in which the 1,3,5,7-tetramethylcyclotetrasiloxane was reduced in functional group by allyl glycidyl ether (Synthesis Comparative Example 3). As a result, although the crack resistance

The invention claimed is:

1. A method for producing a cyclic polyorganosiloxane comprising:
decomposing a polyorganosiloxane by heating the polyorganosiloxane in the presence of a catalyst, the polyorganosiloxane having a main chain skeleton represented by the following general formula (I):

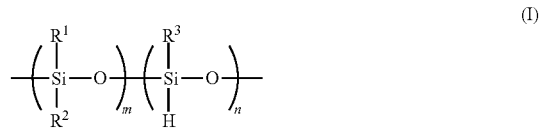

wherein $R^1$ to $R^3$ are identical or different monovalent substituted or unsubstituted hydrocarbon groups; and m and n satisfy:

$0.3 \leq n/(m+n) < 0.9$.

2. The method for producing the cyclic polyorganosiloxane according to claim 1, wherein:
   the polyorganosiloxane is a chain polyorganosiloxane represented by the following general formula (II):

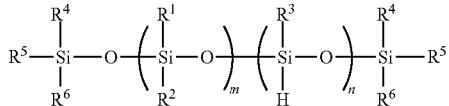
(II)

wherein $R^1$ to $R^3$ are identical or different monovalent substituted or unsubstituted hydrocarbon groups, $R^4$ is a monovalent substituted or unsubstituted hydrocarbon group, $R^5$ is a hydroxyl group or a monovalent substituted or unsubstituted hydrocarbon group, and $R^6$ is a hydrogen atom or a monovalent substituted or unsubstituted hydrocarbon group; m is 1 to 1000, n is 2 to 1000, m and n satisfy:

$4 < m+n < 2000$, and/or, is a cyclic polyorganosiloxane represented by the following general formula (III):

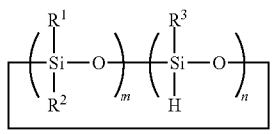
(III)

wherein $R^1$ to $R^3$ are identical or different monovalent substituted or unsubstituted hydrocarbon groups; m is 1 to 1000, n is 2 to 1000, m and n satisfy:

$4 < m+n < 2000$.

3. The method for producing the cyclic polyorganosiloxane according to claim 1, wherein:
   the $R^1$ to $R^3$ in the general formulae (I) to (III) are a methyl group.

4. The method for producing the cyclic polyorganosiloxane according to claim 1, wherein:
   the catalyst has a metal-oxygen bond, and the metal is at least one selected from the group consisting of: aluminum, titanium, zirconium, tin, and zinc.

5. A cyclic polyorganosiloxane obtained by a method recited in claim 1 having the following general formula (IV):

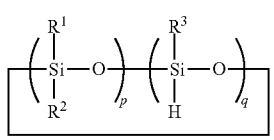
(IV)

wherein $R^1$ to $R^3$ are identical or different monovalent substituted or unsubstituted hydrocarbon groups; p is an integer of 1 to 8, q is an integer of 2 to 6, p and q being integers that satisfy:

$3 \leq p+q \leq 10$.

6. The cyclic polyorganosiloxane according to claim 5, comprising the following compounds (β1) and (β2):

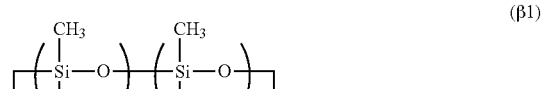
(β1)

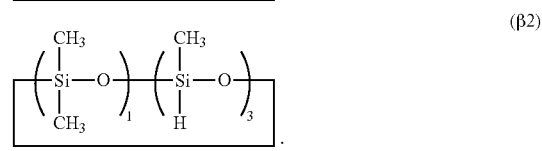
(β2)

7. A modified polyorganosiloxane compound having at least two SiH groups per molecule, the modified polyorganosiloxane compound being a hydrosilylation reaction product of the following compounds:
   (α) an organic compound having two to six carbon-carbon double bonds per molecule, the carbon-carbon double bonds being reactive with an SiH group, and
   (β) a cyclic polyorganosiloxane recited in claim 5.

8. A modified polyorganosiloxane compound having at least two SiH groups per molecule, the modified polyorganosiloxane compound being a hydrosilylation reaction product of the following compounds:
   (α) an organic compound having two to six carbon-carbon double bonds per molecule, the carbon-carbon double bonds being reactive with an SiH group, and
   (β) a cyclic polyorganosiloxane including the following compounds (β1) and (β2):

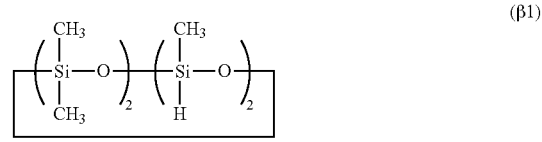
(β1)

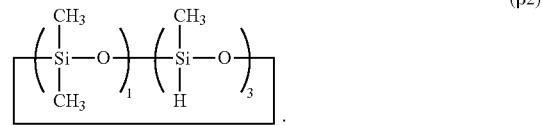
(β2)

9. The modified polyorganosiloxane compound according to claim 7, wherein:
   the (β) cyclic polyorganosiloxane includes the compounds (β1) and (β2) by at least 50 wt % with respect to the total weight of the (β) cyclic polyorganosiloxane.

10. The modified polyorganosiloxane compound according to claim 7, wherein:
    the (α) organic compound is at least one cyclic organic compound selected from the group consisting of: an aromatic compound, an aliphatic cyclic compound, a substituted aliphatic cyclic compound, and a heterocyclic compound.

11. The modified polyorganosiloxane compound according to claim 10, wherein:
    the aromatic compound is divinylbenzene, divinylnaphthalene, divinylbiphenyl, bisphenol-A diallyl ether or bisphenol-S diallyl ether, the aliphatic cyclic compound is cyclopentadiene, cyclohexadiene, cyclooctadiene, dicyclopentadiene, tricyclopentadiene or norbornadiene, the substituted aliphatic cyclic organic compound is vinylcyclopentene, vinylcyclohexene, trivinylcyclohexane, 1,3-bis(allyloxy)adamantane or 1,3,5-tris(allyloxy)adamantane.

12. The modified polyorganosiloxane compound according to claim 7, wherein:
the (α) organic compound includes a compound represented by the following general formula (VI):

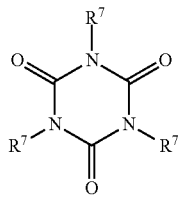

(VI)

wherein $R^7$ is a hydrogen atom or a monovalent organic group having a carbon number of 1 to 50, and at least two $R^7$ groups contain a carbon-carbon double bond, the carbon-carbon double bond being reactive with a SiH group.

13. The modified polyorganosiloxane compound according to claim 7, wherein:
the (α) organic compound includes at least one type thereof selected from the group consisting of: triallyl isocyanurate, monoglycidyl diallyl isocyanurate, and diallyl isocyanurate.

14. A curable composition comprising:
(A) an organic compound having at least two carbon-carbon double bonds per molecule, the carbon-carbon double bond being reactive with a SiH group;
(B) a modified polyorganosiloxane compound; and
(C) a hydrosilylation catalyst, wherein:
the (B) modified polyorganosiloxane compound having at least two SiH groups per molecule and being a hydrosilylation reaction product of the following compounds (α) and (β):
(α) an organic compound having two to six carbon-carbon double bonds per molecule, the carbon-carbon double bonds being reactive with an SiH group, and
(β) a cyclic polyorganosiloxane comprising the following general formula (IV):

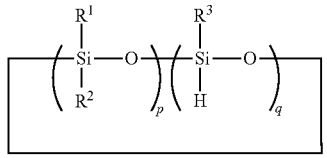

(IV)

wherein $R^1$ to $R^3$ are identical or different monovalent substituted or unsubstituted hydrocarbon groups; p is an integer of 1 to 8, q is an integer of 2 to 6, p and q being integers that satisfy:

$3 \leq p+q \leq 10$;

the cyclic polyorganosiloxane produced by a method comprising:
decomposing a polyorganosiloxane by heating the polyorganosiloxane in the presence of a catalyst, the polyorganosiloxane having a main chain skeleton represented by the following general formula (I):

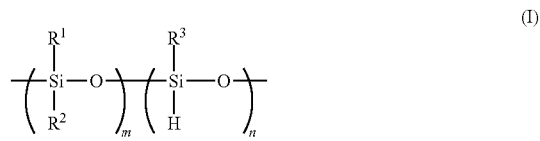

(I)

wherein $R^1$ to $R^3$ are identical or different monovalent substituted or unsubstituted hydrocarbon groups; m and n satisfy:

$0.3 \leq n/(m+n) < 0.9$.

15. The curable composition according to claim 14, wherein:
the (A) organic compound is at least one cyclic organic compound selected from the group consisting of: an aromatic compound, an aliphatic cyclic compound, a substituted aliphatic cyclic compound, and a heterocyclic compound.

16. The curable composition according to claim 15, wherein:
the aromatic compound is divinylbenzene, divinylnaphthalene, divinylbiphenyl, bisphenol-A diallyl ether or bisphenol-S diallyl ether; the aliphatic cyclic compound is cyclopentadiene, cyclohexadiene, cyclooctadiene, dicyclopentadiene, tricyclopentadiene or norbornadiene; and the substituted aliphatic cyclic organic compound is vinylcyclopentene, vinylcyclohexene, trivinylcyclohexane, 1,3-bis(allyloxy)adamantane or 1,3,5-tris(allyloxy)adamantane.

17. The curable composition according to claim 14, wherein:
the (A) organic compound includes a compound represented by the following general formula (VI):

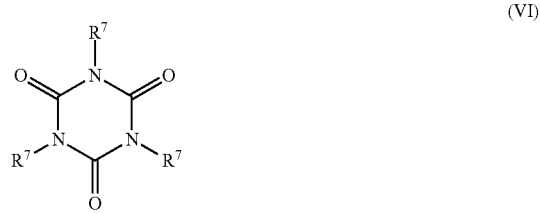

(VI)

wherein $R^7$ is a hydrogen atom or a monovalent organic group having a carbon number of 1 to 50, a plurality of $R^7$ being different or identical to each other, and at least two $R^7$ groups contain a carbon-carbon double bond, the carbon-carbon double bond being reactive with a SiH group.

18. A cured product produced by curing a curable composition recited in claim 14.

19. The curable composition according to claim 14, wherein:
the polyorganosiloxane is a chain polyorganosiloxane represented by the following general formula (II):

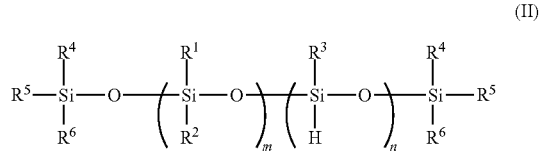

(II)

wherein $R^1$ to $R^3$ are identical or different monovalent substituted or unsubstituted hydrocarbon groups, $R^4$ is a monovalent substituted or unsubstituted hydrocarbon group, $R^5$ is a hydroxyl group or a monovalent substituted or unsubstituted hydrocarbon group, and $R^6$ is a hydrogen atom or a monovalent substituted or unsubstituted hydrocarbon group; m is 1 to 1000, n is 2 to 1000, m and n satisfy:

$4 < m+n < 2000$, and/or, is a cyclic polyorganosiloxane represented by the following general formula (III):

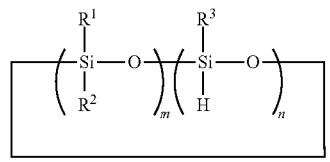

(III)

wherein $R^1$ to $R^3$ are identical or different monovalent substituted or unsubstituted hydrocarbon groups; m is 1 to 1000, n is 2 to 1000, m and n satisfy:

$4 < m+n < 2000$.

20. The curable composition according to claim 19, wherein:
$R^1$ to $R^3$ in the general formulae (I) to (III) are a methyl group.

21. The curable composition according to claim 14, wherein:
the catalyst has a metal-oxygen bond, and the metal is at least one selected from the group consisting of: aluminum, titanium, zirconium, tin, and zinc.

22. The curable composition according to claim 14, comprising the following compounds (β1) and (β2):

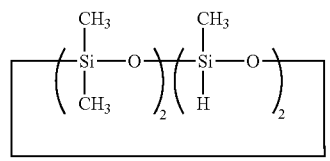

(β1)

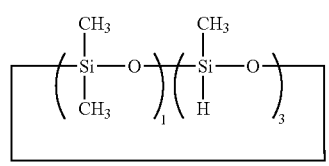

(β2)

23. The curable composition according to claim 14, wherein:
the modified polyorganosiloxane compound having at least two SiH groups per molecule and being a hydrosilylation reaction product of the following compounds:
(α) an organic compound having two to six carbon-carbon double bonds per molecule, the carbon-carbon double bonds being reactive with an SiH group, and (β) a cyclic polyorganosiloxane including the following compounds (β1) and (β2):

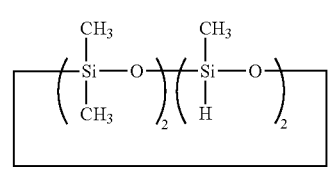

(β1)

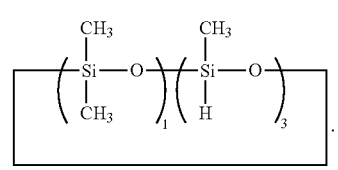

(β2).

24. The curable composition according to claim 23, wherein:
the (β) cyclic polyorganosiloxane includes the compounds (β1) and (β2) by at least 50 wt % with respect to the total weight of the (β) cyclic polyorganosiloxane.

25. The curable composition according to claim 14, wherein:
the (α) organic compound is at least one cyclic organic compound selected from the group consisting of: an aromatic compound, an aliphatic cyclic compound, a substituted aliphatic cyclic compound, and a heterocyclic compound.

26. The curable composition according to claim 25, wherein:
the aromatic compound is divinylbenzene, divinylnaphthalene, divinylbiphenyl, bisphenol-A diallyl ether or bisphenol-S diallyl ether; the aliphatic cyclic compound is cyclopentadiene, cyclohexadiene, cyclooctadiene, dicyclopentadiene, tricyclopentadiene or norbornadiene; and the substituted aliphatic cyclic organic compound is vinylcyclopentene, vinylcyclohexene, trivinylcyclohexane, 1,3-bis(allyloxy)adamantane or 1,3,5-tris(allyloxy)adamantane.

27. The curable composition according to claim 14, wherein:
the (α) organic compound includes a compound represented by the following general formula (VI):

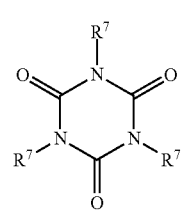

(VI)

wherein $R^7$ is a hydrogen atom or a monovalent organic group having a carbon number of 1 to 50, a plurality of $R^7$ being different or identical to each other, and at least two $R^7$ groups contain a carbon-carbon double bond, the carbon-carbon double bond being reactive with a SiH group.

28. The curable composition according to claim 14, wherein:
the (α) organic compound includes at least one type thereof selected from the group consisting of: triallyl isocyanurate, monoglycidyl diallyl isocyanurate, and diallyl isocyanurate.

* * * * *